United States Patent [19]

Greaves et al.

[11] Patent Number: 5,536,901

[45] Date of Patent: Jul. 16, 1996

[54] HIGH PH TOLERANT CORN AND THE PRODUCTION THEREOF

[75] Inventors: John A. Greaves, Sheldahl; George K. Rufener, II, Johnston, both of Iowa; Raymond J. LeRette, Greeley, Colo.; Martin A. Stoecker, Ames, Iowa

[73] Assignee: Zeneca Limited, London, England

[21] Appl. No.: 286,473

[22] Filed: Aug. 4, 1994

[51] Int. Cl.$^6$ .............................. A01H 5/00; A01H 1/00; C12N 15/00

[52] U.S. Cl. ................ 800/200; 800/250; 800/DIG. 56; 47/58; 47/DIG. 1; 435/172.1; 435/172.3

[58] Field of Search .......................... 800/200; 47/58.03, 47/58.05; 435/172.3

[56] References Cited

PUBLICATIONS

Brady, Nile C., *The Nature and Properties of Soil*, MacMillan, New York, 1974.

Clark, Ralph B., "Iron Deficiency in Plants Grown in the Great Plains of the U.S.", pp. 251–268. *Journal of Plant Nutrition*, vol. 5, No. 3, 1982.

Wallace, Arthur, "Historical Landmarks in Progress Relating to Iron Chlorosis in Plants", pp. 277–288. *Journal of Plant Nutrition*, vol. 5, No. 3, 1982.

Schon et al. (1994) RFLP Mapping in Maize: Quantitative Trait Loci Affecting Testcross Performance of Elite European Flint Lines. Crop Science vol. 34, pp. 378–389.

*Primary Examiner*—Gary Benzion
*Attorney, Agent, or Firm*—Dana Rewoldt

[57] ABSTRACT

This invention relates to a maize plant and a method of producing the same, which is tolerant to high pH soil. More particularly, this invention relates to the introgression in maize of identified genetic material capable of causing the plant to be tolerant to high pH soil. Additionally, the present invention relates to the introgression, with precision and accuracy, of such desired genetic material from one or more parent plants into progeny plants. The present invention also covers the maize plants containing the high pH tolerance material.

7 Claims, 28 Drawing Sheets

FIG. 1

Yield, yield differences, and grain moisture of 24 corn hybrids grown on sodic, calcareous, and two better soil sites in 1992.

| Entry No. | Hybrid | Site 1 Sodic alkali | Diff site 1 vs 2 | Site 2 Calc soil | Diff site 2 vs 3 | Site 3 Good soil | Diff site 3 vs 4 | Site 4 Best soil | Average Moisture |
|---|---|---|---|---|---|---|---|---|---|
| | | ------bu/A------ | | | | | | | % |
| 1. | DeKalb DK501 | 32 | 104 | 136 | 52 | 188 | −4 | 184 | 20.9 |
| 2. | DeKalb DK554 | 115 | 43 | 158 | 49 | 207 | −19 | 188 | 26.3 |
| 3. | GH Ex412 | 117 | 61 | 178 | 29 | 207 | --- | 207 | 32.9 |
| 4. | GH Ex652 | 116 | 32 | 148 | 46 | 194 | +7 | 201 | 26/0 |
| 5. | GH H-2404 | 25 | 98 | 123 | 26 | 149 | +5 | 154 | 20.2 |
| 6. | GH 13069 | 4 | 173 | 177 | 31 | 208 | −11 | 197 | 31.3 |
| 7. | NK N4242 | 81 | 69 | 150 | 22 | 172 | −4 | 168 | 19.7 |
| 8. | NK N6330 | 28 | 137 | 165 | 47 | 212 | −49 | 163 | 30.6 |
| 9. | NK N6873 | 169 | +7 | 162 | 43 | 205 | −7 | 198 | 27.6 |
| 10. | NK N7768 | 85 | 84 | 169 | 43 | 212 | −14 | 198 | 30.2 |
| 11. | NC+ 4275 | 18 | 140 | 158 | 64 | 222 | −35 | 187 | 28.6 |
| 12. | NC+ 5963 | 64 | 110 | 174 | 40 | 214 | −37 | 177 | 32.0 |
| 13. | NC+ 6485 | 104 | 79 | 183 | 22 | 205 | −12 | 193 | 33.1 |
| 14. | NC+ 6959 | 30 | 113 | 143 | 34 | 177 | −23 | 154 | 35.8 |
| 15. | Pioneer 3162 | 105 | 68 | 173 | 52 | 225 | +17 | 242 | 32.4 |
| 16. | Pioneer 3299 | 144 | 32 | 176 | 56 | 232 | −14 | 218 | 33.0 |
| 17. | Pioneer 3245 | 130 | 24 | 154 | 64 | 218 | −1 | 217 | 31.6 |
| 18. | Pioneer 3362 | 129 | 38 | 167 | 38 | 205 | +22 | 227 | 29.3 |
| 19. | Pioneer 3398 | 9 | 139 | 148 | 54 | 202 | +29 | 231 | 29.8 |
| 20. | Pioneer 3394 | 106 | 72 | 178 | 48 | 226 | −5 | 221 | 28.5 |
| 21. | Pioneer 3417 | 2 | 163 | 165 | 52 | 217 | −8 | 209 | 28.3 |
| 22. | Pioneer 3563 | 11 | 159 | 170 | 49 | 219 | −38 | 181 | 22.5 |
| 23. | Crows 488 | 161 | 15 | 176 | 28 | 204 | −10 | 194 | 28.5 |
| 24. | A634 × N193[1] | 146 | +25 | 121 | 13 | 134 | −6 | 128 | 20.1 |
| Mean | | 80 | 80 | 160 | 42 | 202 | −9 | 193 | 28.3 |
| cv% | | 40 | | 12 | | 9 | | 15 | |
| LSD 0.05 | | 11 | | 22 | | 20 | | 34 | |
| LSD 0.01 | | 13 | | 29 | | 27 | | 41 | |

[1]Very poor stands of this hybrid in sites 2, 3, and 4 may have limited yield of this entry on those sites.

FIG. 2B

| Relative chlorophyll content on inbreds grown in high pH field (location 8311), Nebraska | | | | |
|---|---|---|---|---|
| entry # | mean | std error | n= | score |
| 1 | 11.18889 | 1.268958 | 18 | 4 |
| 2 | 14.09259 | 1.211271 | 27 | 2 |
| 3 | 14.68095 | 0.942581 | 21 | 3 |
| 4 | 15.5125 | 1.297843 | 24 | 4 |
| 5 | 16.405 | 1.17102 | 20 | 5 |
| 6 | 17.16 | 1.129191 | 30 | 4 |
| 7 | 18.46 | 0.9134 | 25 | 4 |
| 8 | 18.67179 | 1.407757 | 39 | 3 |
| 9 | 19.00455 | 1.299742 | 22 | 5 |
| 10 | 19.0439 | 1.069756 | 41 | 4 |
| 11 | 20.36944 | 1.194424 | 36 | 3 |
| 12 | 20.55429 | 1.062448 | 35 | 4 |
| 13 | 20.56429 | 1.313523 | 14 | 6 |
| 14 | 20.6375 | 1.395929 | 24 | 4 |
| 15 | 22.1619 | 1.220314 | 21 | 4 |
| 16 | 22.24 | 1.372795 | 25 | 3 |
| 17 | 22.79655 | 1.046358 | 29 | 4 |
| 18 | 23.09091 | 0.950937 | 22 | 6 |
| 19 | 23.5129 | 1.26222 | 31 | 4 |
| 20 | 23.77407 | 1.394266 | 27 | 6 |
| 21 | 23.82727 | 1.699111 | 22 | 5 |
| 22 | 24.15862 | 1.020969 | 29 | 5 |
| 23 | 24.38 | 1.911125 | 10 | 5 |
| 24 | 25.13478 | 1.33644 | 23 | 4 |
| 25 | 25.15333 | 1.424633 | 30 | 5 |
| 26 | 25.27037 | 0.877915 | 27 | 4 |
| 27 | 25.7 | 1.136946 | 17 | |
| 28 | 25.85588 | 1.092636 | 34 | 5 |
| 29 | 26.44595 | 0.887692 | 37 | 4 |
| 30 | 26.50909 | 0.874473 | 33 | 5 |
| 31 | 26.59259 | 2.398996 | 27 | 3 |
| 32 | 26.73947 | 1.048127 | 38 | 5 |
| 33 | 27 | 0.689848 | 33 | 6 |
| 34 | 27.11842 | 0.965197 | 38 | 6 |
| 35 | 27.15135 | 1.000443 | 38 | 4 |
| 36 | 27.34375 | 2.073865 | 16 | 6 |
| 37 | 28.02857 | 0.639925 | 42 | 6 |
| 38 | 28.1425 | 0.640552 | 40 | 5 |
| 39 | 28.16923 | 2.148416 | 13 | 4 |
| 40 | 28.46053 | 1.088858 | 38 | 5 |
| 41 | 28.62692 | 1.090202 | 26 | 4 |
| 42 | 28.64138 | 1.11243 | 29 | 6 |
| 43 | 28.75128 | 1.371015 | 40 | 5 |
| 44 | 29.22308 | 1.262433 | 13 | 6 |
| 45 | 29.3 | 1.115224 | 34 | 6 |
| 46 | 29.41111 | 1.231904 | 27 | 4 |
| 47 | 29.52 | 1.277356 | 15 | 7 |
| 48 | 29.58889 | 1.222421 | 36 | 5 |
| 49 | 29.59167 | 2.179153 | 12 | 5 |
| 50 | 29.80682 | 0.646065 | 45 | 5 |

FIG. 2C

| Relative cholorophyll content on inbreds grown in high pH field (location 8311), Nebraska | | | | |
|---|---|---|---|---|
| entry # | mean | std error | n= | score |
| 51 | 29.888 | 1.777426 | 25 | 6 |
| 52 | 29.92 | 1.644458 | 20 | 5 |
| 53 | 30.04324 | 0.910025 | 37 | 5 |
| 54 | 30.1 | 1.316195 | 26 | 6 |
| 55 | 30.25758 | 0.997526 | 33 | 5 |
| 56 | 30.31282 | 1.023761 | 39 | 5 |
| 57 | 30.39333 | 0.960327 | 30 | 6 |
| 58 | 30.4069 | 1.070989 | 29 | 6 |
| 59 | 30.41707 | 0.805764 | 41 | 5 |
| 60 | 30.465 | 0.85017 | 40 | 5 |
| 61 | 30.48261 | 1.012621 | 23 | 5 |
| 62 | 30.50513 | 0.833565 | 39 | 5 |
| 63 | 30.61481 | 1.223566 | 27 | 6 |
| 64 | 30.635 | 0.863904 | 20 | 7 |
| 65 | 30.68 | 1.300884 | 35 | 6 |
| 66 | 30.75294 | 1.012817 | 34 | 6 |
| 67 | 30.81522 | 0.737648 | 46 | 5 |
| 68 | 31.1925 | 0.757242 | 40 | 6 |
| 69 | 31.33056 | 1.043421 | 36 | 6 |
| 70 | 31.35652 | 0.791727 | 23 | 5 |
| 71 | 31.36316 | 1.197639 | 19 | 6 |
| 72 | 31.3875 | 0.788094 | 40 | 6 |
| 73 | 31.41795 | 1.149957 | 39 | 6 |
| 74 | 31.42571 | 0.713535 | 35 | 7 |
| 75 | 31.43333 | 1.43564 | 21 | 6 |
| 76 | 31.59 | 1.289554 | 30 | 6 |
| 77 | 31.63704 | 1.099756 | 27 | 5 |
| 78 | 31.98276 | 0.671501 | 29 | 6 |
| 79 | 32.06 | 1.943491 | 10 | 6 |
| 80 | 32.35758 | 0.952091 | 33 | 6 |
| 81 | 32.52174 | 0.881966 | 23 | 7 |
| 82 | 32.53462 | 0.819304 | 26 | 5 |
| 83 | 32.57692 | 0.958799 | 37 | 6 |
| 84 | 32.61333 | 0.939953 | 15 | 6 |
| 85 | 32.66 | 0.968975 | 45 | 6 |
| 86 | 32.69778 | 0.678304 | 45 | 6 |
| 87 | 32.776 | 1.194631 | 25 | 6 |
| 88 | 32.81667 | 0.937447 | 30 | 6 |
| 89 | 32.84444 | 1.376466 | 36 | 7 |
| 90 | 32.96667 | 0.998841 | 21 | 6 |
| 91 | 32.97234 | 0.51392 | 47 | 6 |
| 92 | 33.15172 | 0.953211 | 29 | 7 |
| 93 | 33.156 | 1.59826 | 25 | 6 |
| 94 | 33.38 | 0.797705 | 25 | 7 |
| 95 | 33.63721 | 0.442809 | 43 | 7 |
| 96 | 33.67368 | 1.124835 | 19 | 5 |
| 97 | 33.67826 | 1.192002 | 23 | 6 |
| 98 | 33.78261 | 0.826811 | 46 | 7 |
| 99 | 33.83 | 0.407463 | 30 | 6 |
| 100 | 33.89459 | 0.836489 | 37 | 6 |

FIG. 2D

| Relative cholorophyll content on inbreds grown in high pH field (location 8311), Nebraska | | | | |
|---|---|---|---|---|
| entry # | mean | std error | n= | score |
| 101 | 33.91951 | 0.943988 | 41 | 6 |
| 102 | 34.43939 | 1.124604 | 33 | 6 |
| 103 | 34.44865 | 0.883016 | 38 | 5 |
| 104 | 34.4625 | 1.179103 | 24 | 7 |
| 105 | 34.49375 | 1.186573 | 16 | 5 |
| 106 | 34.57143 | 1.376644 | 21 | 6 |
| 107 | 34.61951 | 0.732189 | 41 | 7 |
| 108 | 34.68571 | 0.794137 | 28 | 6 |
| 109 | 34.70263 | 0.577217 | 38 | 5 |
| 110 | 34.91818 | 1.078351 | 22 | 5 |
| 111 | 34.92381 | 1.046671 | 21 | 6 |
| 112 | 34.96667 | 0.94824 | 36 | 8 |
| 113 | 35.03158 | 0.750174 | 38 | 6 |
| 114 | 35.055 | 0.723063 | 40 | 7 |
| 115 | 35.14667 | 1.733696 | 15 | 7 |
| 116 | 35.39032 | 1.035118 | 31 | 5 |
| 117 | 35.41852 | 1.058799 | 27 | 7 |
| 118 | 35.59615 | 1.302571 | 26 | 7 |
| 119 | 35.62143 | 0.594034 | 14 | 6 |
| 120 | 35.79444 | 0.78875 | 36 | 6 |
| 121 | 35.81667 | 0.711153 | 36 | 8 |
| 122 | 36.08462 | 0.847652 | 26 | 6 |
| 123 | 36.27381 | 0.835758 | 43 | 7 |
| 124 | 36.31053 | 0.656197 | 38 | 6 |
| 125 | 36.35 | 1.07879 | 30 | 6 |
| 126 | 36.375 | 0.71009 | 40 | 7 |
| 127 | 36.46129 | 1.096972 | 31 | 6 |
| 128 | 36.49583 | 0.927313 | 24 | 6 |
| 129 | 36.50741 | 1.272937 | 27 | 6 |
| 130 | 36.53333 | 1.151511 | 33 | 6 |
| 131 | 36.5375 | 0.853399 | 24 | 6 |
| 132 | 36.60909 | 0.974012 | 33 | 6 |
| 133 | 36.67838 | 0.731325 | 37 | 7 |
| 134 | 36.68788 | 0.972313 | 33 | 7 |
| 135 | 37.03556 | 0.884034 | 45 | 7 |
| 136 | 37.04583 | 1.133498 | 24 | 7 |
| 137 | 37.29063 | 0.593978 | 32 | 6 |
| 138 | 37.3 | 0.903881 | 16 | 7 |
| 139 | 37.35926 | 1.042928 | 27 | 6 |
| 140 | 37.36579 | 0.781109 | 38 | 7 |
| 141 | 37.40244 | 0.773088 | 41 | 7 |
| 142 | 37.42308 | 1.242755 | 26 | 6 |
| 143 | 37.45349 | 0.804537 | 43 | 6 |
| 144 | 37.46 | 0.655096 | 40 | 6 |
| 145 | 37.50732 | 0.851537 | 41 | 7 |
| 146 | 37.5125 | 0.828291 | 40 | 7 |
| 147 | 37.59091 | 1.541042 | 11 | 7 |
| 148 | 37.62857 | 0.976952 | 21 | 6 |
| 149 | 37.68 | 0.794773 | 30 | 7 |
| 150 | 37.695 | 0.639571 | 40 | 7 |

FIG. 2E

| Relative cholorophyll content on inbreds grown in high pH field (location 8311), Nebraska | | | | |
|---|---|---|---|---|
| entry # | mean | std error | n= | score |
| 151 | 37.87407 | 0.709311 | 27 | 6 |
| 152 | 37.97273 | 1.52471 | 33 | 7 |
| 153 | 38.105 | 0.698055 | 40 | 7 |
| 154 | 38.35526 | 1.174823 | 38 | 7 |
| 155 | 38.46364 | 1.477077 | 22 | 7 |
| 156 | 38.51111 | 0.701795 | 27 | 6 |
| 157 | 38.6525 | 0.628786 | 40 | 7 |
| 158 | 38.86 | 0.593296 | 25 | 7 |
| 159 | 38.86571 | 0.659054 | 35 | 6 |
| 160 | 38.97143 | 0.722995 | 21 | 7 |
| 161 | 39.0186 | 0.737534 | 43 | 7 |
| 162 | 39.10263 | 0.997746 | 38 | 7 |
| 163 | 39.38 | 0.953224 | 35 | 6 |
| 164 | 39.63636 | 0.735141 | 33 | 8 |
| 165 | 39.88718 | 0.513399 | 39 | 6 |
| 166 | 40 | 1.304558 | 19 | 7 |
| 167 | 40.01538 | 1.025377 | 39 | 6 |
| 168 | 40.05 | 1.085277 | 24 | 7 |
| 169 | 40.535 | 0.60233 | 40 | 7 |
| 170 | 40.59677 | 0.832453 | 31 | 9 |
| 171 | 40.62973 | 0.650074 | 37 | 7 |
| 172 | 40.65152 | 0.773313 | 33 | 7 |
| 173 | 40.72059 | 0.730794 | 34 | 7 |
| 174 | 40.80526 | 0.84086 | 19 | 7 |
| 175 | 40.90417 | 0.857141 | 24 | 7 |
| 176 | 40.94688 | 0.887196 | 32 | 6 |
| 177 | 41.11538 | 1.292327 | 13 | 8 |
| 178 | 41.364 | 1.494321 | 25 | 8 |
| 179 | 41.40588 | 0.743 | 34 | 7 |
| 180 | 41.59048 | 0.704398 | 42 | 7 |
| 181 | 41.61351 | 0.62372 | 37 | 6 |
| 182 | 41.80667 | 1.041175 | 15 | 6 |
| 183 | 42.025 | 0.845336 | 28 | 7 |
| 184 | 42.0587 | 0.73741 | 46 | 7 |
| 185 | 42.6575 | 0.888674 | 40 | 7 |
| 186 | 42.73953 | 1.029548 | 43 | 7 |
| 187 | 42.79778 | 0.457821 | 46 | 9 |
| 188 | 43.01333 | 0.514208 | 45 | 7 |
| 189 | 43.10294 | 0.563293 | 34 | 7 |
| 190 | 43.17647 | 0.558519 | 34 | 7 |
| 191 | 43.43 | 0.813918 | 30 | 7 |
| 192 | 44.83889 | 0.735713 | 36 | 8 |
| 193 | 44.87778 | 0.931146 | 36 | 7 |
| 194 | 45.26061 | 0.851102 | 33 | 8 |
| 195 | 52.08462 | 0.738881 | 39 | 9 |

Relationship between mean relative chlorophyll content of 195 inbred lines grouped by visual high pH score (best-fit line)

FIG. 10A

| High pH field study of F4 families: Mean relative chlorophyll content | | | | | | | | |
|---|---|---|---|---|---|---|---|---|
| Measurements taken at Gering (8311) 7/12/94 with SPAD-502 chlorophyll meters | | | | | | | | |
| Measurements taken at Yuma (6230) 7/14/94 with SPAD-502 chlorophyll meters | | | | | | | | |
| Entry # | Gering | Yuma | Entry # | Gering | Yuma | Entry # | Gering | Yuma |
| Sensitive | 14.85 | 11.25 | 30 | 33 | 17.25 | 61 | 35 | 22.8 |
| Tolerant | 43.75 | 40.3 | 31 | 27.65 | 16.85 | 62 | 33.75 | 24 |
| 1 | 34.9 | 23.35 | 32 | 27.25 | 14.65 | 63 | 38.15 | 28.9 |
| 2 | 31.05 | 21.55 | 33 | 33.3 | 28.1 | 64 | 31.95 | 24.85 |
| 3 | 40.7 | 31.25 | 34 | 28.75 | 19.95 | 65 | 36.45 | 23.65 |
| 4 | 36.45 | 23.65 | 35 | 29.2 | 19.45 | 66 | 36.85 | 25.65 |
| 5 | 32.15 | 23.1 | 36 | 27.85 | 22.1 | 67 | 26.4 | 17.85 |
| 6 | 31.75 | 25.6 | 37 | 30.05 | 18.8 | 68 | 31.95 | 20.95 |
| 7 | 35.05 | 23.15 | 38 | 29.8 | 18.7 | 69 | 29.2 | 19.8 |
| 8 | 36.4 | 26.85 | 39 | 35.1 | 22.5 | 70 | 37.15 | 24 |
| 9 | 32.3 | 23.35 | 40 | 34.4 | 20.05 | 71 | 43.9 | 36.1 |
| 10 | 36.1 | 29.15 | 41 | 35.7 | 28.6 | 72 | 34 | 29.3 |
| 11 | 34.05 | 29.4 | 42 | 32.9 | 25.15 | 73 | 35.25 | 26.75 |
| 12 | 39 | 32.65 | 43 | 39.15 | 33.7 | 74 | 31.65 | 20.7 |
| 13 | 23.95 | 16.4 | 44 | 27.15 | 19.8 | 75 | 33.45 | 21.2 |
| 14 | 31.4 | 23.85 | 45 | 22.85 | 12.5 | 76 | 36.1 | 25.15 |
| 15 | 36.6 | 29.7 | 46 | 26.25 | 17 | 77 | 28.55 | 19.3 |
| 16 | 37.65 | 31 | 47 | 26.95 | 22.65 | 78 | 29.35 | 19.9 |
| 17 | 30.1 | 20.25 | 48 | 27.2 | 21.3 | 79 | 35.85 | 32.7 |
| 18 | 34.75 | 28.1 | 49 | 25.55 | 18 | 80 | 23.2 | 19.2 |
| 19 | 36.7 | 27.35 | 50 | 29.05 | 23.4 | 81 | 29.5 | 22.25 |
| 20 | 30.15 | 21.25 | 51 | 25.55 | 19.45 | 82 | 37.05 | 29.25 |
| 21 | 33.5 | 25.55 | 52 | 36.7 | 28.9 | 83 | 34.95 | 24 |
| 22 | 35.5 | 26.9 | 53 | 32.15 | 27.75 | 84 | 21.7 | 15.65 |
| 23 | 39.1 | 31.75 | 54 | 37.75 | 29.5 | 85 | 35.7 | 26.3 |
| 24 | 31.65 | 24.3 | 55 | 32.6 | 26.55 | 86 | 32.2 | 21.35 |
| 25 | 31.4 | 24.85 | 56 | 38.9 | 33.8 | 87 | 35.45 | 24.2 |
| 26 | 33.15 | 28.2 | 57 | 39.2 | 28.6 | 88 | 39.2 | 28.05 |
| 27 | 36.3 | 26.25 | 58 | 41.1 | 30.7 | 89 | 33.1 | 23.5 |
| 28 | 31.55 | 25.25 | 59 | 28.15 | 20.25 | 90 | 35.55 | 26.8 |
| 29 | 32.25 | 21.7 | 60 | 26.85 | 19.65 | 91 | 36.5 | 26.7 |

FIG. 10B

| High pH field study of F4 families: Mean relative chlorophyll content |||||||||
|---|---|---|---|---|---|---|---|---|
| Measurements taken at Gering (8311) 7/12/94 with SPAD-502 chlorophyll meters |||||||||
| Measurements taken at Yuma (6230) 7/14/94 with SPAD-502 chlorophyll meters |||||||||
| Entry # | Gering | Yuma | Entry # | Gering | Yuma | Entry # | Gering | Yuma |
| 92 | 35.1 | 26.2 | 120 | 44.4 | 28.8 | 148 | 35.85 | 24.65 |
| 93 | 30.75 | 22.2 | 121 | 38.1 | 26.8 | 149 | 34.7 | 27.3 |
| 94 | 36 | 27.4 | 122 | 38 | 29.6 | 150 | 27.65 | 21.3 |
| 95 | | | 123 | 31.5 | 19.35 | 151 | 35.65 | 31.9 |
| 96 | 39.3 | 29.95 | 124 | 29.9 | 17.4 | 152 | 29.4 | 23.35 |
| 97 | 36.25 | 26 | 125 | 25.35 | 15.2 | 153 | 31.7 | 19.9 |
| 98 | 28.15 | 21.55 | 126 | 29 | 21.2 | 154 | 33.75 | 25.05 |
| 99 | 41.95 | 23.95 | 127 | 31.4 | 28.15 | 155 | 33.15 | 27.1 |
| 100 | 34.3 | 27.75 | 128 | 32.4 | 25.45 | 156 | 25.25 | 21.4 |
| 101 | 36.4 | 27.3 | 129 | 31.75 | 26.65 | 157 | 28.05 | 21.15 |
| 102 | 37.25 | 24.8 | 130 | 31.8 | 26.65 | 158 | 38.1 | 32.5 |
| 103 | 34.7 | 25.8 | 131 | 31.25 | 29.85 | 159 | 40.45 | 33 |
| 104 | 35.2 | 24.85 | 132 | 37.75 | 33.7 | 160 | 22.35 | 18.15 |
| 105 | 37.9 | 25 | 133 | 37.15 | 31.2 | 161 | 33.55 | 26.25 |
| 106 | 26.75 | 19.7 | 134 | 28.3 | 16.8 | 162 | 33.35 | 29.4 |
| 107 | 31.7 | 28.9 | 135 | 40.4 | 26.9 | 163 | 30.2 | 23.5 |
| 108 | 35.6 | 24.7 | 136 | 37.45 | 26.55 | 164 | 36.85 | 32.9 |
| 109 | 33 | 24.9 | 137 | 34.1 | 28.05 | 165 | 31.35 | 27.95 |
| 110 | 36.8 | 24 | 138 | 36.4 | 25.45 | 166 | 40.8 | 36.55 |
| 111 | 34.25 | 27.15 | 139 | 38.75 | 24.95 | 167 | 37.6 | 30.2 |
| 112 | 37.5 | 23 | 140 | 37.95 | 32.95 | 168 | 32.55 | 24.85 |
| 113 | 36.05 | 27.8 | 141 | 41.4 | 28.6 | 169 | 37.4 | 30.7 |
| 114 | 37.35 | 30.05 | 142 | 35.35 | 30 | 170 | 26.55 | 19.4 |
| 115 | 37.5 | 28.15 | 143 | 27.75 | 20.6 | 171 | 32.15 | 20.9 |
| 116 | 35.7 | 28.35 | 144 | 34.8 | 23.8 | 172 | 32.2 | 28.5 |
| 117 | 36.75 | 24.15 | 145 | 34.4 | 28.9 | 173 | 26.6 | 16.45 |
| 118 | 39.15 | 30 | 146 | | | 174 | 27.85 | 21.2 |
| 119 | 29.6 | 19.2 | 147 | 17.2 | 12.05 | 175 | 25.8 | 19.55 |

FIG. 11

MAIZE CHROMOSOME 3

BNL815 UMC121 CSU16 BNL8.35 NPI247 UMC102 BNL5.37 NPI296 UMC60 BNL6.16 BNL3.18 NPI432 UMC63 UMC96 UMC2A
UMC32 UMC92 NPI446 UMC10 NPI279B NPI108 CSU38 UMC18 UMC82 UMC16

HpH1    HpH2

MAIZE CHROMOSOME 5

B8.33 NPI409 UMC90 UMC27 BNL6.22 BNL4.36 BNL7.71 ALS2 BNL5.71 UMC126 UMC51 UMC108 NPI288
BNL6.25 UMC1 NPI233 NPI424 NPI1449 NPI1295 NPI1239 NPI1562 NPI1458 NPI1442 UMC68

HpH3

MAIZE CHROMOSOME 6

UMC85 NPI393 NPI396B BNL6.06B NPI252 UMC38 NPI280 UMC132
BNL6.29 NPI101 UMC59 NPI373 UMC62

HpH4

FIG. 12

HIPH DATA

R = YU0244        S

MEANRCC = MEAN OF 2 LOCS, 2 REPS EACH - AT GERING AND YUMA

| CHROM | MAP# | MEANRCC ||||| CHROM | MAP# | MEANRCC |||||
|---|---|---|---|---|---|---|---|---|---|---|---|---|---|
| | | SIG | PR>F | RSQ | FALC A | PR>T | | | SIG | PR>F | RSQ | FALC A | PR>T |
| 3 | B0318 B | 5 | 0.04 | 0.04 | 0.86 | 0.15 | 5 | U0001 B | | 0.63 | 0.01 | 0.50 | 0.34 |
| 3 | U0092 B | 0 | 0.00 | 0.14 | 2.44 | 0.00 | 5 | B0622 A | | 0.13 | 0.02 | 0.99 | 0.04 |
| 3 | N0446 B | 0 | 0.00 | 0.15 | 2.50 | 0.00 | 5 | N0233 A | 5 | 0.02 | 0.06 | 1.39 | 0.01 |
| 3 | B0835 A | 0 | 0.00 | 0.17 | 2.69 | 0.00 | 5 | B0436 B | 5 | 0.01 | 0.06 | 1.48 | 0.01 |
| 3 | U0010 A | 0 | 0.00 | 0.31 | 3.39 | 0.00 | 5 | N0424 A | | 0.39 | 0.02 | 1.00 | 0.18 |
| 3 | U0102 A | 0 | 0.00 | 0.29 | 3.12 | 0.00 | 5 | B0771 B | 5 | 0.01 | 0.05 | 1.44 | 0.00 |
| 3 | N0279 A | 0 | 0.00 | 0.24 | 3.02 | 0.00 | 5 | N0449 E | 1 | 0.00 | 0.08 | 1.67 | 0.00 |
| 3 | U0018 D | 0 | 0.00 | 0.20 | 2.72 | 0.00 | 5 | ALS95AB | 0 | 0.00 | 0.09 | 1.78 | 0.00 |
| 3 | U0026BA | 0 | 0.00 | 0.23 | 1.82 | 0.00 | 5 | N0295 A | 1 | 0.00 | 0.07 | 1.59 | 0.00 |
| 3 | U0026 A | 0 | 0.00 | 0.21 | 2.65 | 0.00 | 5 | B0571 A | 5 | 0.01 | 0.05 | 1.15 | 0.01 |
| 3 | B0537 E | 0 | 0.00 | 0.18 | 2.26 | 0.00 | 5 | N0239 D | | 0.14 | 0.02 | 1.01 | 0.05 |
| 3 | N0108 B | 0 | 0.00 | 0.25 | 3.05 | 0.00 | 5 | U0126 A | | 0.21 | 0.02 | 0.78 | 0.08 |
| 3 | N0296 B | 0 | 0.00 | 0.21 | 2.95 | 0.00 | 5 | U0051 D | | 0.28 | 0.02 | 0.77 | 0.12 |
| 3 | U0329UA | 0 | 0.00 | 0.16 | 2.61 | 0.00 | 5 | ALS95BB | | 0.59 | 0.01 | 0.38 | 0.46 |
| 3 | U0060 B | 0 | 0.00 | 0.10 | 2.13 | 0.00 | 5 | U0108 B | | 0.19 | 0.19 | -2.69 | 0.10 |
| 3 | U0082 A | | 0.06 | 0.29 | 1.96 | 0.11 | 5 | N0442 D | | 0.17 | 0.02 | 0.60 | 0.18 |
| 3 | B0616 B | 0 | 0.00 | 0.10 | 2.03 | 0.00 | 5 | N0288 B | | 0.52 | 0.01 | 0.17 | 0.72 |
| 3 | U0017AD | | 0.15 | 0.02 | 0.69 | 0.14 | 5 | U0068 B | | 0.54 | 0.01 | -0.02 | 0.98 |
| 3 | U0016 B | | 0.52 | 0.01 | 0.04 | 0.94 | 5 | N0458 B | | 0.60 | 0.01 | 0.48 | 0.32 |
| 3 | N0432 A | | 0.54 | 0.01 | 0.49 | 0.29 | 5 | N0562 A | 1 | 0.01 | 0.06 | 0.79 | 0.08 |
| 3 | U0327 B | | 0.82 | 0.00 | -0.33 | 0.53 | 6 | B0629 A | 5 | 0.02 | 0.05 | 0.70 | 0.16 |
| 3 | N0457 B | | 0.65 | 0.01 | -0.45 | 0.37 | 6 | U0085 A | | 0.29 | 0.02 | 0.66 | 0.13 |
| 3 | N0425 B | | 0.73 | 0.00 | -0.40 | 0.42 | 6 | I0103 D | | 0.33 | 0.02 | 0.62 | 0.25 |
| 4 | N0594 B | | 0.97 | 0.00 | -0.05 | 0.92 | 6 | N0101 A | 5 | 0.04 | 0.04 | 1.17 | 0.01 |
| 4 | I0104 B | | 0.95 | 0.00 | 0.16 | 0.74 | 6 | N0373 B | 1 | 0.00 | 0.08 | 1.60 | 0.00 |
| 4 | B1545 B | | 0.24 | 0.02 | -0.54 | 0.25 | 6 | U0059 B | | 0.09 | 0.03 | 1.02 | 0.03 |
| 4 | N0396 A | | 0.77 | 0.00 | -0.05 | 0.93 | 6 | N0393 E | | 0.13 | 0.02 | 0.92 | 0.05 |
| 4 | U0026AA | | 0.63 | 0.01 | -0.06 | 0.92 | 6 | N0396 B | | 0.25 | 0.02 | 0.70 | 0.13 |
| 4 | N0584 B | | 0.28 | 0.02 | 0.40 | 0.38 | 6 | B0606 B | | 0.06 | 0.09 | 1.90 | 0.02 |
| 4 | U0066 D | | 0.37 | 0.01 | -0.18 | 0.72 | 6 | N0252 B | 1 | 0.01 | 0.06 | 1.40 | 0.01 |
| 4 | U0019 D | | 0.24 | 0.02 | -0.11 | 0.83 | 6 | U0038 B | 5 | 0.02 | 0.05 | 1.36 | 0.00 |
| 4 | N0270 D | | 0.17 | 0.02 | 0.46 | 0.37 | 6 | N0280 B | | 0.78 | 0.00 | 0.31 | 0.54 |
| 4 | U0015 B | | 0.20 | 0.02 | -0.24 | 0.65 | | | | | | | |
| 4 | U0052 B | | 0.55 | 0.01 | -0.27 | 0.68 | | | | | | | |
| 4 | N0444 B | | 0.56 | 0.01 | -0.29 | 0.59 | | | | | | | |
| 5 | U0090 E | | 0.35 | 0.01 | -0.66 | 0.17 | | | | | | | |
| 5 | U0027 A | | 0.44 | 0.01 | 0.63 | 0.21 | | | | | | | |

SIGNIFICANCE LEVEL SCORES
    NO SCORE = NOT SIGNIFICANT AT THE .05 LEVEL
    5 = SIGNIFICANT AT THE .05 LEVEL
    1 = SIGNIFICANT AT THE .01 LEVEL
    0 = SIGNIFICANT AT A LEVEL LOWER THAN .01
    - = ANALYSIS NOT AVAILABLE (GENOTYPE MAY BE THE SAME FOR
        ALL ENTRIES OR THERE MAY ONLY 1 OBSERVATION PER CLASS)

FIG. 13A

HIPH DATA

R = YU0244    S

MEANRCC = MEAN OF 2 LOCS, 2 REPS EACH - AT GERING AND YUMA

| U0036_B | | MEANRCC | | | U0102_A | | MEANRCC | |
|---|---|---|---|---|---|---|---|---|
| GENOTYPE | MEAN | STD ERR | N | | GENOTYPE | MEAN | STD ERR | N |
| RR | 27.87 | 0.70 | 38 | | RR | 31.48 | 0.57 | 44 |
| RS | 29.68 | 0.49 | 78 | | RS | 29.90 | 0.42 | 80 |
| SS | 28.61 | 0.65 | 44 | | SS | 25.23 | 0.57 | 45 |

| B0318_B | | MEANRCC | | | N0279_A | | MEANRCC | |
|---|---|---|---|---|---|---|---|---|
| GENOTYPE | MEAN | STD ERR | N | | GENOTYPE | MEAN | STD ERR | N |
| RR | 29.16 | 0.88 | 26 | | RR | 31.43 | 0.63 | 40 |
| RS | 29.76 | 0.47 | 93 | | RS | 29.34 | 0.45 | 78 |
| SS | 27.44 | 0.77 | 34 | | SS | 25.38 | 0.63 | 39 |

| U0092_B | | MEANRCC | | | U0018_D | | MEANRCC | |
|---|---|---|---|---|---|---|---|---|
| GENOTYPE | MEAN | STD ERR | N | | GENOTYPE | MEAN | STD ERR | N |
| RR | 30.78 | 0.69 | 37 | | RR | 31.29 | 0.64 | 38 |
| RS | 29.49 | 0.45 | 86 | | RS | 29.55 | 0.44 | 79 |
| SS | 25.90 | 0.75 | 31 | | SS | 25.84 | 0.67 | 35 |

| N0446_B | | MEANRCC | | | U0026BA | | MEANRCC | |
|---|---|---|---|---|---|---|---|---|
| GENOTYPE | MEAN | STD ERR | N | | GENOTYPE | MEAN | STD ERR | N |
| RR | 31.46 | 0.69 | 37 | | RR | 28.98 | 0.70 | 31 |
| RS | 29.32 | 0.47 | 80 | | RS | 30.59 | 0.41 | 90 |
| SS | 26.47 | 0.69 | 37 | | SS | 25.33 | 0.64 | 37 |

| B0835_A | | MEANRCC | | | U0026_A | | MEANRCC | |
|---|---|---|---|---|---|---|---|---|
| GENOTYPE | MEAN | STD ERR | N | | GENOTYPE | MEAN | STD ERR | N |
| RR | 31.53 | 0.63 | 41 | | RR | 30.47 | 0.49 | 65 |
| RS | 29.23 | 0.42 | 93 | | RS | 29.74 | 0.51 | 59 |
| SS | 26.15 | 0.65 | 39 | | SS | 25.17 | 0.71 | 31 |

| U0010_A | | MEANRCC | | | B0537_E | | MEANRCC | |
|---|---|---|---|---|---|---|---|---|
| GENOTYPE | MEAN | STD ERR | N | | GENOTYPE | MEAN | STD ERR | N |
| RR | 31.81 | 0.59 | 40 | | RR | 29.98 | 0.60 | 47 |
| RS | 29.79 | 0.40 | 88 | | RS | 30.05 | 0.47 | 78 |
| SS | 25.04 | 0.56 | 44 | | SS | 25.46 | 0.70 | 35 |

FIG. 13B

HIPH DATA

R = YU0244    S

MEANRCC = MEAN OF 2 LOCS, 2 REPS EACH - AT GERING AND YUMA

| N0108_B GENOTYPE | MEAN | MEANRCC STD ERR | N |
|---|---|---|---|
| RR | 31.26 | 0.65 | 37 |
| RS | 29.92 | 0.43 | 85 |
| SS | 25.16 | 0.64 | 39 |

| U0017AD GENOTYPE | MEAN | MEANRCC STD ERR | N |
|---|---|---|---|
| RR | 29.36 | 0.66 | 43 |
| RS | 29.56 | 0.48 | 81 |
| SS | 27.99 | 0.67 | 42 |

| N0296_B GENOTYPE | MEAN | MEANRCC STD ERR | N |
|---|---|---|---|
| RR | 31.24 | 0.67 | 36 |
| RS | 29.56 | 0.40 | 99 |
| SS | 25.34 | 0.66 | 37 |

| U0016_B GENOTYPE | MEAN | MEANRCC STD ERR | N |
|---|---|---|---|
| RR | 28.75 | 0.79 | 33 |
| RS | 29.61 | 0.60 | 57 |
| SS | 28.68 | 0.69 | 43 |

| U0329UA GENOTYPE | MEAN | MEANRCC STD ERR | N |
|---|---|---|---|
| RR | 31.55 | 0.89 | 22 |
| RS | 28.81 | 0.57 | 53 |
| SS | 26.32 | 0.85 | 24 |

| N0432_A GENOTYPE | MEAN | MEANRCC STD ERR | N |
|---|---|---|---|
| RR | 29.75 | 0.62 | 49 |
| RS | 29.08 | 0.50 | 77 |
| SS | 28.77 | 0.68 | 41 |

| U0060_B GENOTYPE | MEAN | MEANRCC STD ERR | N |
|---|---|---|---|
| RR | 31.05 | 0.71 | 36 |
| RS | 29.25 | 0.44 | 93 |
| SS | 26.78 | 0.71 | 36 |

| U0327_B GENOTYPE | MEAN | MEANRCC STD ERR | N |
|---|---|---|---|
| RR | 28.79 | 0.60 | 53 |
| RS | 28.97 | 0.48 | 83 |
| SS | 29.46 | 0.88 | 25 |

| U0082_A GENOTYPE | MEAN | MEANRCC STD ERR | N |
|---|---|---|---|
| RR | 30.05 | 1.54 | 5 |
| RS | 31.34 | 1.09 | 10 |
| SS | 26.13 | 1.72 | 4 |

| N0457_B GENOTYPE | MEAN | MEANRCC STD ERR | N |
|---|---|---|---|
| RR | 28.60 | 0.66 | 48 |
| RS | 29.15 | 0.55 | 70 |
| SS | 29.49 | 0.75 | 37 |

| B0616_B GENOTYPE | MEAN | MEANRCC STD ERR | N |
|---|---|---|---|
| RR | 31.29 | 0.72 | 37 |
| RS | 29.28 | 0.50 | 76 |
| SS | 27.23 | 0.70 | 39 |

| N0425_B GENOTYPE | MEAN | MEANRCC STD ERR | N |
|---|---|---|---|
| RR | 28.69 | 0.71 | 43 |
| RS | 29.11 | 0.55 | 70 |
| SS | 29.50 | 0.72 | 42 |

FIG. 13C

HIPH DATA

R = YU0244    S

MEANRCC = MEAN OF 2 LOCS, 2 REPS EACH - AT GERING AND YUMA

| U0090_E | | MEANRCC | | N0424_A | | MEANRCC | |
|---|---|---|---|---|---|---|---|
| GENOTYPE | MEAN | STD ERR | N | GENOTYPE | MEAN | STD ERR | N |
| RR | 28.25 | 0.73 | 35 | RR | 29.44 | 1.03 | 20 |
| RS | 29.32 | 0.49 | 78 | RS | 28.71 | 0.72 | 41 |
| SS | 29.57 | 0.61 | 50 | SS | 27.44 | 1.05 | 19 |

| U0027_A | | MEANRCC | | B0771_B | | MEANRCC | |
|---|---|---|---|---|---|---|---|
| GENOTYPE | MEAN | STD ERR | N | GENOTYPE | MEAN | STD ERR | N |
| RR | 29.62 | 0.74 | 36 | RR | 30.69 | 0.69 | 40 |
| RS | 29.16 | 0.47 | 90 | RS | 29.00 | 0.48 | 81 |
| SS | 28.35 | 0.69 | 41 | SS | 27.81 | 0.65 | 44 |

| U0001_B | | MEANRCC | | N0449_E | | MEANRCC | |
|---|---|---|---|---|---|---|---|
| GENOTYPE | MEAN | STD ERR | N | GENOTYPE | MEAN | STD ERR | N |
| RR | 29.56 | 0.74 | 36 | RR | 31.11 | 0.77 | 28 |
| RS | 29.02 | 0.46 | 92 | RS | 29.79 | 0.45 | 81 |
| SS | 28.56 | 0.73 | 37 | SS | 27.76 | 0.64 | 41 |

| B0622_A | | MEANRCC | | ALS95AB | | MEANRCC | |
|---|---|---|---|---|---|---|---|
| GENOTYPE | MEAN | STD ERR | N | GENOTYPE | MEAN | STD ERR | N |
| RR | 29.84 | 0.67 | 44 | RR | 31.12 | 0.66 | 44 |
| RS | 29.09 | 0.48 | 87 | RS | 28.71 | 0.52 | 73 |
| SS | 27.85 | 0.71 | 39 | SS | 27.56 | 0.68 | 42 |

| N0233_A | | MEANRCC | | N0295_A | | MEANRCC | |
|---|---|---|---|---|---|---|---|
| GENOTYPE | MEAN | STD ERR | N | GENOTYPE | MEAN | STD ERR | N |
| RR | 30.30 | 0.68 | 43 | RR | 30.76 | 0.62 | 48 |
| RS | 28.61 | 0.67 | 44 | RS | 28.78 | 0.49 | 79 |
| SS | 27.51 | 0.75 | 36 | SS | 27.57 | 0.65 | 44 |

| B0436_B | | MEANRCC | | B0571_A | | MEANRCC | |
|---|---|---|---|---|---|---|---|
| GENOTYPE | MEAN | STD ERR | N | GENOTYPE | MEAN | STD ERR | N |
| RR | 30.95 | 0.74 | 37 | RR | 30.71 | 0.66 | 44 |
| RS | 28.71 | 0.49 | 84 | RS | 28.45 | 0.49 | 79 |
| SS | 27.99 | 0.74 | 37 | SS | 28.41 | 0.64 | 47 |

FIG. 13D

HIPH DATA

R = YU0244    S

MEANRCC = MEAN OF 2 LOCS, 2 REPS EACH - AT GERING AND YUMA

| N0239_D | | MEANRCC | |
|---|---|---|---|
| GENOTYPE | MEAN | STD ERR | N |
| RR | 30.32 | 0.76 | 33 |
| RS | 29.07 | 0.48 | 83 |
| SS | 28.31 | 0.66 | 44 |

| N0288_B | | MEANRCC | |
|---|---|---|---|
| GENOTYPE | MEAN | STD ERR | N |
| RR | 29.00 | 0.70 | 40 |
| RS | 29.57 | 0.52 | 74 |
| SS | 28.66 | 0.63 | 49 |

| U0126_A | | MEANRCC | |
|---|---|---|---|
| GENOTYPE | MEAN | STD ERR | N |
| RR | 29.88 | 0.69 | 42 |
| RS | 29.11 | 0.54 | 68 |
| SS | 28.32 | 0.57 | 61 |

| U0068_B | | MEANRCC | |
|---|---|---|---|
| GENOTYPE | MEAN | STD ERR | N |
| RR | 28.66 | 0.80 | 31 |
| RS | 29.45 | 0.49 | 83 |
| SS | 28.69 | 0.66 | 45 |

| U0051_D | | MEANRCC | |
|---|---|---|---|
| GENOTYPE | MEAN | STD ERR | N |
| RR | 30.05 | 0.77 | 33 |
| RS | 29.25 | 0.56 | 62 |
| SS | 28.51 | 0.61 | 52 |

| N0458_B | | MEANRCC | |
|---|---|---|---|
| GENOTYPE | MEAN | STD ERR | N |
| RR | 29.74 | 0.69 | 41 |
| RS | 29.11 | 0.52 | 73 |
| SS | 28.78 | 0.65 | 46 |

| ALS95BB | | MEANRCC | |
|---|---|---|---|
| GENOTYPE | MEAN | STD ERR | N |
| RR | 29.66 | 0.72 | 42 |
| RS | 28.71 | 0.62 | 56 |
| SS | 28.89 | 0.74 | 40 |

| N0562_A | | MEANRCC | |
|---|---|---|---|
| GENOTYPE | MEAN | STD ERR | N |
| RR | 29.33 | 0.74 | 34 |
| RS | 30.03 | 0.55 | 61 |
| SS | 27.74 | 0.50 | 73 |

| U0108_B | | MEANRCC | |
|---|---|---|---|
| GENOTYPE | MEAN | STD ERR | N |
| RR | 24.48 | 2.57 | 4 |
| RS | 30.35 | 2.10 | 6 |
| SS | 29.86 | 1.72 | 9 |

| B0629_A | | MEANRCC | |
|---|---|---|---|
| GENOTYPE | MEAN | STD ERR | N |
| RR | 29.02 | 0.76 | 33 |
| RS | 29.83 | 0.46 | 88 |
| SS | 27.62 | 0.63 | 48 |

| N0442_D | | MEANRCC | |
|---|---|---|---|
| GENOTYPE | MEAN | STD ERR | N |
| RR | 30.42 | 0.68 | 39 |
| RS | 28.82 | 0.51 | 69 |
| SS | 29.22 | 0.58 | 55 |

| U0085_A | | MEANRCC | |
|---|---|---|---|
| GENOTYPE | MEAN | STD ERR | N |
| RR | 29.81 | 0.59 | 58 |
| RS | 28.93 | 0.62 | 53 |
| SS | 28.49 | 0.62 | 52 |

FIG. 13E

HIPH DATA

R = YU0244        S

MEANRCC = MEAN OF 2 LOCS, 2 REPS EACH - AT GERING AND YUMA

I0103_D

| GENOTYPE | MEAN | MEANRCC STD ERR | N |
|---|---|---|---|
| RR | 29.62 | 0.66 | 45 |
| RS | 29.95 | 0.68 | 42 |
| SS | 29.37 | 0.85 | 27 |

B0606_B

| GENOTYPE | MEAN | MEANRCC STD ERR | N |
|---|---|---|---|
| RR | 30.22 | 1.22 | 13 |
| RS | 28.73 | 0.82 | 29 |
| SS | 26.41 | 1.07 | 17 |

N0101_A

| GENOTYPE | MEAN | MEANRCC STD ERR | N |
|---|---|---|---|
| RR | 29.73 | 0.57 | 59 |
| RS | 29.12 | 0.50 | 76 |
| SS | 27.40 | 0.74 | 35 |

N0252_B

| GENOTYPE | MEAN | MEANRCC STD ERR | N |
|---|---|---|---|
| RR | 30.84 | 0.67 | 43 |
| RS | 28.61 | 0.46 | 91 |
| SS | 28.04 | 0.79 | 31 |

N0373_B

| GENOTYPE | MEAN | MEANRCC STD ERR | N |
|---|---|---|---|
| RR | 29.95 | 0.56 | 61 |
| RS | 29.50 | 0.52 | 71 |
| SS | 26.75 | 0.72 | 36 |

U0038_B

| GENOTYPE | MEAN | MEANRCC STD ERR | N |
|---|---|---|---|
| RR | 30.09 | 0.62 | 48 |
| RS | 28.99 | 0.49 | 75 |
| SS | 27.38 | 0.70 | 37 |

U0059_B

| GENOTYPE | MEAN | MEANRCC STD ERR | N |
|---|---|---|---|
| RR | 29.90 | 0.61 | 51 |
| RS | 29.16 | 0.54 | 65 |
| SS | 27.87 | 0.69 | 40 |

N0280_B

| GENOTYPE | MEAN | MEANRCC STD ERR | N |
|---|---|---|---|
| RR | 29.44 | 0.71 | 38 |
| RS | 29.35 | 0.49 | 81 |
| SS | 28.82 | 0.69 | 40 |

N0393_E

| GENOTYPE | MEAN | MEANRCC STD ERR | N |
|---|---|---|---|
| RR | 29.63 | 0.57 | 60 |
| RS | 29.31 | 0.53 | 71 |
| SS | 27.80 | 0.74 | 36 |

U0062_A

| GENOTYPE | MEAN | MEANRCC STD ERR | N |
|---|---|---|---|
| RR | 28.69 | 0.66 | 46 |
| RS | 29.69 | 0.50 | 79 |
| SS | 28.40 | 0.66 | 45 |

N0396_B

| GENOTYPE | MEAN | MEANRCC STD ERR | N |
|---|---|---|---|
| RR | 30.13 | 0.63 | 51 |
| RS | 28.98 | 0.57 | 61 |
| SS | 28.74 | 0.67 | 45 |

CHROMOSOME 3

CHROMOSOME 3 CONT.

CHROMOSOME 5

CHROMOSOME 5 CONT.

CHROMOSOME 6

CHROMOSOME 6 CONT.

HIGH PH TOLERANT CORN AND THE PRODUCTION THEREOF

FIELD OF THE INVENTION

This invention relates to a maize plant and a method of producing same, which is tolerant (which is defined as a plant having normal height and at least 75% of the normal seed formation for the same genotype in other than high pH soil) to high pH soil which will hereinafter simply be referred to HpH soil. More particularly this invention relates to the introgression in maize of identifying genetic material capable of causing the plant to be tolerant to high pH soil. Additionally, the present invention relates to the introgression of a desired genetic material from one or more parent plants into progeny plants with precision and accuracy.

BACKGROUND OF THE INVENTION

Historically maize (corn) has been used as a source of food for human and animal consumption. Even today maize supplies about twenty percent of the world's calories. Any environmental stress factor that affects a large proportion of the maize growing regions can have a substantial impact on the quantity of maize annually available for consumption. Thus reduction of the sensitivity associated with HpH is understandably of great importance since approximately 10–12 million corn growing acres are affected by high pH (basic) soil. Therefore the development of high pH soil tolerant maize is the subject of interest to many commercial corn breeding programs. It is known in the industry that HpH soil has detrimental effects on the hybrids yield potential. Professors Paul Nordquist and Gary Hergert, Professors of Agronomy, did a corn pH tolerance study in 1992 on corn hybrids in calcareous and alkali soils and the following FIG. 1 gives their results. FIG. 1 clearly evidences the loss in yield associated with calcareous soil.

High pH (basic) soils are prevalent throughout the North Central and Western corn belt. The HpH (greater than 7.5 pH) of the soil arises due to a predominantly calcareous bed-rock, combined with low rainfall and relatively low organic matter in the soil. The high pH results in maize plants having an induced iron (Fe) deficiency syndrome. Most corn grown in high pH soil has a syndrome that is expressed visually in sensitive genotypes as stunting, yellowing of leaves, reduced dry matter accumulation, sterility or severely delayed pollen shed, poor silk development, and reduced yield. The HpH syndrome appears to be a result of the maize plant's inability to utilize the necessary nutrients from HpH soil particularly iron.

Although when tested many high pH soils appear to have the basic nutrients necessary for the growth and development of the maize plant. Even in soils that do not have all of the necessary nutrients, addition of the nutrients to high pH soils does not appear to result in a reduction of the high pH syndrome. Suggesting that it is not the availability of the nutrients per se but the ability of the plant to assimilate the nutrient under conditions of HpH.

Although iron (Fe) is a major component of most soils, it exists as silicates, oxides and hydroxides, and is sparingly soluble in well aerated soils, even at low pH. It has been demonstrated that $Fe^{3+}$ (the form of iron used by plants), has exceedingly low solubility in soils of pH 7.0 and above; and that Fe solubility decreases by three orders of magnitude for every unit increase in pH. The syndrome of high pH stress can be compounded by bicarbonates in the soil solution or irrigation water, reduced soil aeration, cool temperatures and high light intensities.

To date there are some fairly high pH tolerant maize hybrids that have been developed by traditional breeding methods. Unfortunately, it is difficult to transfer this tolerance to new inbreds and additionally it is difficult to transfer it to new hybrid products. In fact, it is quite common to see some poor agronomic traits and loss of tolerance associated with moving the tolerance trait from inbred to inbred.

Heretofore, few if any, truly agronomically desirable varieties of the corn in the hybrids have tolerance to high pH soil and also have the necessary agronomic traits for commercial production. Given that pursuant to this invention it has been discovered four genes, three of high significance control the maize plant's response to high pH, a progeny containing these genes, one of which is recessive, within a genome is expected to be a very rare occurrence. The presence of the four newly discovered alleles in the same genome is a very rare occurrence.

One of the fundamental principles of maize breeding is a production of a hybrid having the desired mix of traits by the combination of two inbreds. Getting the correct mix of traits in two inbreds to produce a hybrid especially when traits are not directly associated with a phenotype characteristic of a plant can be difficult. To produce improved hybrids, there is an ongoing development of new inbreds. An inbred is a plant which has become homozygous at almost all loci. There are two primary germplasm sources for producing new inbreds. One source is germplasm that has been genetically engineered; the second source is an adapted or an unadapted germplasm.

In a conventional breeding program, pedigree breeding and recurrent selection breeding methods are employed to develop new inbred lines with desired resistant traits. Maize breeding programs attempt to develop these inbred lines by self-pollinating plants and selecting the desirable plants from the populations. An inbred produces a uniform population of hybrid plants when crossed with a second homozygous line, i.e., inbred. Inbreds tend to have poor vigor and low yield; however, the progeny of an inbred cross usually evidences vigor. The progeny of a cross between two inbreds is often identified as an $F_1$ hybrid. The resultant $F_1$ hybrids which may be heterozygous at a number of loci, are evaluated to determine whether or not they show the tolerance trait and agronomically important and desirable traits. Identification of desirable agronomic traits has typically been done by breeders' expertise. A plant breeder identifies a desired trait for the area in which his plants are to be grown and selects inbreds which appear to pass the desirable trait or traits on to the hybrid.

Conventional plant breeders rely on phenotypic traits of the inbreds for selection purposes. Modern plant breeding technology looks at the genotypic material (chromosomes) for plant breeding purposes. One method of looking at plant genotypes is to use Restriction Fragment Length Polymorphisms (RFLPs) which provide a method for identifying the chromosomal regions which affect the agronomic traits in the plant genome which the plant breeder is attempting to introgress into the inbred line for ultimate expression in the hybrid.

RFLPs can be used to identify chromosomal regions in maize which is a ten chromosome plant. Each chromosome has a short arm with a distal and proximal end and a long arm having a distal and proximal end. Between the short arm proximal end and long arm proximal end is a centromere. Each chromosome is made up of strands of the deoxyribonucleic acid (DNA) molecule which has a specific nucleic acid sequence. Selected restriction endonucleases will identify a specific base sequence and cleave the DNA molecule wherever this sequence occurs. The resultant cleaved portions are called restriction fragments. These restriction fragments can be separated by size by electrophoresis through agarose gels.

The DNA of two individual maize plants will differ in sequence at a variety of sites. Because of this difference, restriction endonucleases may cleave an individual's DNA at a different site or location than the other individual's DNA. A polymorphism in the length of restriction fragments is produced when the fragments of the two individuals have different lengths. A polymorphism is detected by placing the fragments on an agarose gel electrophoresis and allowing them to separate by size over distance. A southern blot is then used. The fragments of the DNA are physically transferred on to a membrane, then nucleic acid hybridization detects the sequences by hybridization of the single strand of DNA (probe) on the southern blot. The nucleic acid reforms double stranded DNA. A radio labelled probe is used to detect a particular (DNA) sequence. One method is to use a labelled probe such that the DNA fragment will be identifiable through autoradiography techniques.

A variety of maize genes have been mapped and identified using RFLPs. Certain polymorphisms (molecular markers) are used to identify chromosomal areas associated with certain traits. A large number of molecular markers including RFLPs have been applied to the maize genome and a detailed maize genetic linkage map that can be used to localize important genes has been constructed.

A variety of traits have been identified by RFLPs; for example, P1 pericarp color has been linked to UMC185 (P1) on the short arm of chromosome one of the maize plant. Probes BNL6.29 and UMC85 on chromosome six of the maize plant have been identified with Maize Dwarf Mosaic Virus (MDMV) strain A resistance in maize. Likewise, a variety of other traits have been genetically identified and placed on the maize genetic linkage map.

It would appear that once a desired trait is recognized and the gene chromosome region expressing that trait is located between flanking probes in a maize plant by the use of RFLPs, that the trait should be readily introgressed into an inbred line. Unfortunately, it is not easy to recognize the desired gene location and although RFLPs are a tool which can be employed to help identify the chromosomal region to which the trait appears to be linked, RFLPs are not a solution in and of themselves. RFLPs are simply a tool of identification. It should be noted that the chromosomal regions associated with high pH tolerance have not been previously mapped or identified using probes.

Almost nothing has hitherto been known about the genes responsible for tolerance to high pH. The number of genes involved, their action, where they are located on the maize chromosome have not been identified. There is a need for the identification of the location of genes associated with tolerance to high pH which permits their tracking when introgressed into new plants through traditional breeding. There also remains a need for a method of transferring tolerance to high pH soil to a corn inbred that has desirable agronomic traits. There remains a need for tolerant high pH inbreds and hybrids.

SUMMARY OF THE INVENTION

An object of the present invention is to provide a maize line which exhibits tolerance to high pH soil and maintains other agronomically desirable traits in hybrid combination.

A further object of the invention is to provide a commercially viable high pH tolerant hybrid.

Yet another object of the present invention is to provide a breeding method to identify and track chromosomal regions in plants to develop tolerance to high pH soils.

Broadly then the present invention is an improved inbred maize line, being derived from a first parent which evidences a tolerance to high pH soil and a second parent which evidences a susceptibility to high pH soil and has germplasm with desirable yield and moisture characteristics when in non-high pH soil, and wherein the improved inbred line has the tolerance to high pH soil, not significantly less than that of the first parent and yield and moisture characteristics evidenced in high pH soils which are not significantly less than those of the second parent.

Furthermore, the present invention includes an elite inbred maize plant, and parts thereof exhibiting tolerance to high comprising a genome which is homologous in respect to genes within identifiable chromosome regions conferring tolerance to high pH and genes specifying desirable agronomic traits when in hybrid combination, the genome being entirely of maize origin.

More specifically then the present invention encompasses a maize plant tolerance to high pH soil, the genome which contains genes associated with exceptional tolerance of high pH at, one or more loci selected from the group consisting of: (locus 1) chromosome 3, between map unit 61 and map unit 83. This position appears to coincide with the yellow stripe 3 mutant location hereinafter YS3: (locus 2) chromosome 3, map unit 98 and 106; (locus 3) chromosome 5, map unit 95 and map unit 103; (locus 4) chromosome 6, map unit 9 through map unit 20; references to map units and chromosomal location being references to the chromosome map published for the 1993 Maize Genetics Cooperation Newsletter Mar. 15, 1993, at FIG. 14.

Additionally, the present invention is related to the production of hybrids using converted inbreds or progeny of the converted inbreds. Thus the present invention includes a maize hybrid plant, or plants parts of the plant progeny of a the cross between first and second inbred lines, at least one of the inbred lines being a converted line, with the genes conferring tolerance to high pH soil being present in homologous state in the genome of one or the other or both of the first and second inbred lines such that the genome of the first and second inbred lines together donate to the hybrid a complement of high pH genes necessary to confer the tolerance to high pH soil to the hybrid.

The present invention further includes a method for production of inbred maize plants adapted for conferring, in hybrid combination with a suitable second inbred, tolerance to high pH soil. The method includes the steps of first selecting a donor parent line possessing the desired high pH tolerance trait and crossing the same with an elite, high yielding second parental line to produce a segregating population. Then screening the plant population for identified chromosomal loci have one or more genes associated with the tolerant trait; selecting from the population having the identified chromosomal loci for further crossing and selection, and repeating the crossing and selection until the line is obtained which is homozygous for the tolerance trait at the selective loci and has the necessary elite, high yielding genotype to give agronomically acceptable characteristics in hybrid combination.

The present invention further includes the inbred YU0244 which is tolerant to HpH.

These and other objects of the present invention will become more readily appreciated and understood from a consideration of the following detailed description of the preferred embodiment when taken together with the accompanying drawings, in which:

BRIEF DESCRIPTIONS OF THE DRAWINGS

FIG. 1 shows (prior art) a test comparing various hybrids in high pH soil (hybrids may be identified by trademarks of the listed companies.) and in good soil;

FIGS. 2A, 2B, 2C, 2D, 2E shows the mean relative chlorophyll content of 195 inbreds and shows the RCC and the visual score given each inbred;

FIGS. 10A, 10B shows RCC measurement from individual YU0244/S $F_4$ families at HpH locations in Colorado (Yuma) and Nebraska (Gering);

FIG. 11 shows the chromosomal regions associated with the four HpH genes;

FIG. 12 is a table of data indicating the magnitude of statistical significance of the rating score differences of homozygous RFLP genotypes for each of adjacent RFLP probes;

FIGS. 13A, 13B, 13C, 13D, 13E is a table of data developed for each probe site denoting the rating for each genotype of the progeny of a resistant YU0244=R by susceptible S; and FIGS. 14A, 14B, 14C, 14D, 14E, 14F is a map portion listing probes for the chromosomes of the maize plant. The map shown is from the map published by the 1993 Maize Genetics Cooperation NewsLetter published Mar. 15, 1993, by Department of Agronomy and U.S. Department of Agriculture, University of Missouri, Columbia, Mo.

DETAILED DESCRIPTION OF THE EMBODIMENTS

Broadly this invention relates to a maize plant and a method of producing the same, which is tolerant to high pH soil. This invention relates to the introgression in maize of genetic material (for the first time identified) which is capable of causing the plant to be tolerant to high pH soil. Additionally the present invention relates to method of introgression of the desired genetic material from one or more parent plants into the progeny with precision and accuracy. Specifically the present invention relates to a plant that is high pH tolerant to what is commonly referred as white dirt (calcareous soil). The present invention is believed to be tolerant to alkali soil. It should be appreciated that the high pH tolerant converted line offers a much improved donor for use in pedigree or backcrossing programs because recombination for genes for yield and other desirable agronomic traits have already been accomplished by the present invention. To assist in the description of this invention the following glossary of terms are provided.

Converted Plant—any plant having tolerance to high pH soil and additionally the plant or an ancestor of the plant was or has been selected by reference to RFLP data for at least one of the loci herein defined as 1–3.

Crossover—shall mean an exchange of segments of homologous chromosomes during meiosis whereby linked genes become recombined; also the product of such an exchange. The cross-over frequency is the proportion of gametes bearing a cross-over between two specific gene loci. It generally ranges from 0 for allelic genes to 50% for genes so far apart that there is always a cross-over between them. The cross-over site is the place in the chromosome where breakage and reunion of DNA strands occur during recombination.

Figure 2A:
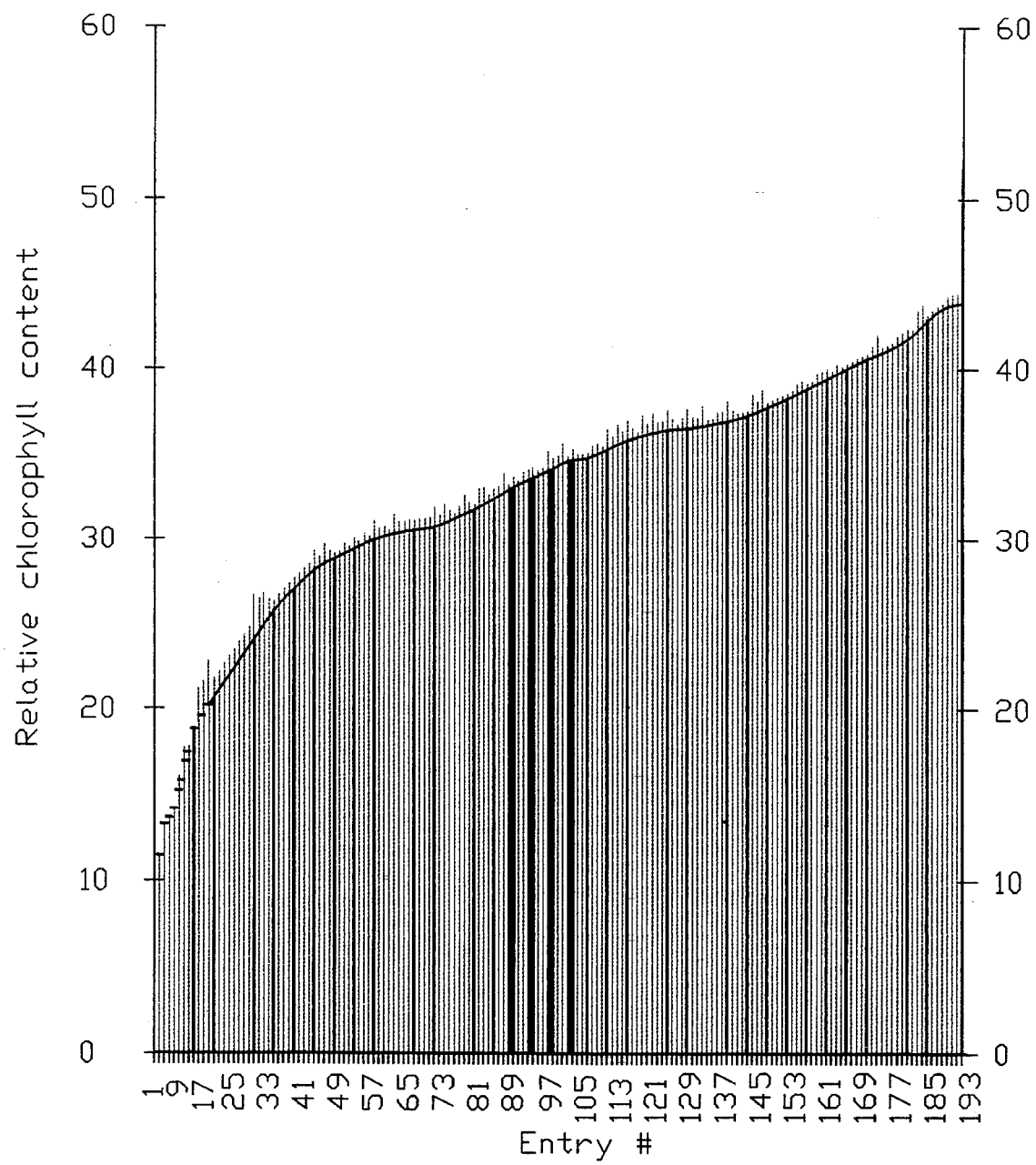

Exceptional tolerance—RCC levels significantly higher than the average RCC levels of maize growing in HpH soil (see FIG. 2).

Introgression—shall mean the entry or introduction of a gene or a linkage block from one plant into another.

Introgressing—shall mean entering or introducing a gene or a linkage block from one plant into another.

Linkage Block—shall mean an identified chromosomal region containing genetic material that expresses a desired trait.

Recombination—shall mean reassortment of genes or characters in combinations different from what they were in the parents, in the case of linked genes by crossing over.

The method of the present invention comprises of use of molecular markers to select progeny from a cross between a high pH tolerant donor and a high yielding, susceptible recipient whose progeny contains all or most of the preferred alleles for high pH tolerant maize and many agronomically desirable traits. It is not necessary and often inefficient to find the complete complement among the progeny of a first cross. However, it is possible to select individual progeny plants exhibiting a proportion of the desired recombinations and to further cross or backcross such individuals in order to create the desired genome progressively.

The donor parent is preferably line designated YU0244 (deposited in the ATCC on Aug. 22, 1994 having deposit number 75869) or its progenitors or resistant progeny containing the loci 1 through 4 (described below) which are detectable by RFLP or equivalent molecular marker analysis. The donor of the high pH tolerant resistant genetic material used in the present invention is a proprietary line of ICI SEEDS which was developed by years of selective breeding for the HpH tolerant trait. Applicant, (from a deposit maintained prior to Aug. 4, 1994, by ICI Seeds, at Slater, Iowa,) has deposited with the American Type Culture Collection (ATCC), Rockville, Md. 20852, U.S.A. on Aug. 22, 1994, at least 2,500 seeds of Inbred Corn Line YU0244. This deposit of YU0244 has ATCC Accession No. 75869. This deposit of YU0244 will be maintained in the depository for a period of 30 years, or 5 years after the most recent request, or the life of the patent, whichever is longer, and will be replaced, in this period, if it becomes nonviable. The seed has been tested by the depository as viable on Aug. 26, 1994. Applicant does not waive its rights under the patent law or PVP Act, but Applicant imposes no restriction on the availability of the deposited material from the ATCC. Other sources of this genetic material will of course be located since the present invention now allows this material to be identified. Additionally the identified chromosome region can readily be analyzed by use of a yac library or other gene library to identity and specifically sequence the genes. These genes can then be used in a cloning protocol for introgression into new plants by transformation techniques such as particle bombardment, whiskers or microprojectile introduction or Agrobacteruim.

The present invention has the entire yield/agronomic/pH tolerant package and includes a method of using modern breeding technique to move the desirable genetic material from one elite background to other elite backgrounds or from germplasm source material to elite backgrounds, etc.

This invention was developed in two stages. The first stage was the location of the chromosomal regions containing genes that characterize that plant as expressing tolerance to high pH soil. The second stage was the introgression of the identified chromosomal region into a genotype that has agronomically desirable traits.

Historically tolerance assessment of HpH soil on plants has been based on visual observation and in some studies on the yield results and yield differences. The present invention was developed using a newly developed visual scoring scale as shown in Table 1.

Table 1: High pH Scoring Scale

1.=Death (the plant may reach a height of 30 cm, with heavy chlorosis and eventual death)

2.=White/Yellow (the plant may reach 60 cm, vegetative only, no shoot or tassel development)

3.=white→Yellow (the plant may reach 90 cm, shoot not viable, very small main axis tassel)

4.=Yellow (short in stature, shoot/tassel developed, poor nick, no or little grain development)

5.=Yellow/Green striping (close to normal height, problem with nick 5–7 days)

6.=Pale Green/some striping (close to normal height, nick close to normal, seed formed)

7.=Green/little striping (normal height, close to normal seed formation)

8.=Green (normal growth and development, good seed set)

9.=Dark Green (darker green than "8", some visual advantage, and more stable, normal seed set)

This type of assessment was not as precise a measurement of the plants reaction as was desired. Thus, a new assessment procedure was employed to assess the plants' response to the HpH stress based on a measurement of relative chlorophyll content (RCC).

There was a little concern about the accuracy of measuring RCC using the SPAD-502 instrument(commercially available from Minolta) because of it's measuring area. The measuring area is extremely small and was sometimes difficult to get an accurate integrated measurement of RCC in a leaf which was striping green and yellow. In an attempt to alleviate this problem, a new instrument was designed in cooperation with Opti-Sciences Inc. (commercially available under Tm "OSAM") Tweksbury, Mass.

The principle of the system was relatively simple. The instrument remotely senses the relative amount of chlorophyll present by measuring the ratio of transmittance of two wavelengths of light through the leaf tissue. One wavelength (RED) is absorbed by chlorophyll and serves as the detection source, while the other wavelength (INFRA-RED) is relatively unaffected by the presence of chlorophyll, and serves as a reference for tissue density variations. The RCC value represents the ratio of transmittance with an adjusting constant compensating for variances in the source output, and mechanical shifts in the sample clip.

The instrument's optical design was optimized to provide the optimum averaging over the sample area to allow for more accurate measurement of RCC on leaf tissue exhibiting localized pigment anomalies. The sample area seals around the top and bottom of the leaf tissue and forms a modified integrating sphere. A very high degree of randomization between the source and detector image is created, which allows for position insensitivity of spots in the measuring window. Radiation for the measurement is provided by solid state LED sources. A set of silicon photodiodes provide the basis of the light detection method. Both the radiation source and detection hardware are housed in the sample head. The photodiode signal is processed by a custom amplifier circuit that provides a detection range in the order of 5 decades of transmittance (50 relative points). The sources are controlled and all the calculations made in the hand-held datalogger pod.

In order to confirm the value of measuring relative chlorophyll content to quantify high pH tolerance/sensitivity, a field study was set up at a location in western Nebraska. Due to the high pH level of the soil, it provided an ideal location to differentiate lines for their relative tolerance/sensitivity to high pH soils. Although the location was on a high pH site, the severity of the stress was not considered to be as high as at the Yuma (CO) high pH location.

Figure 3:
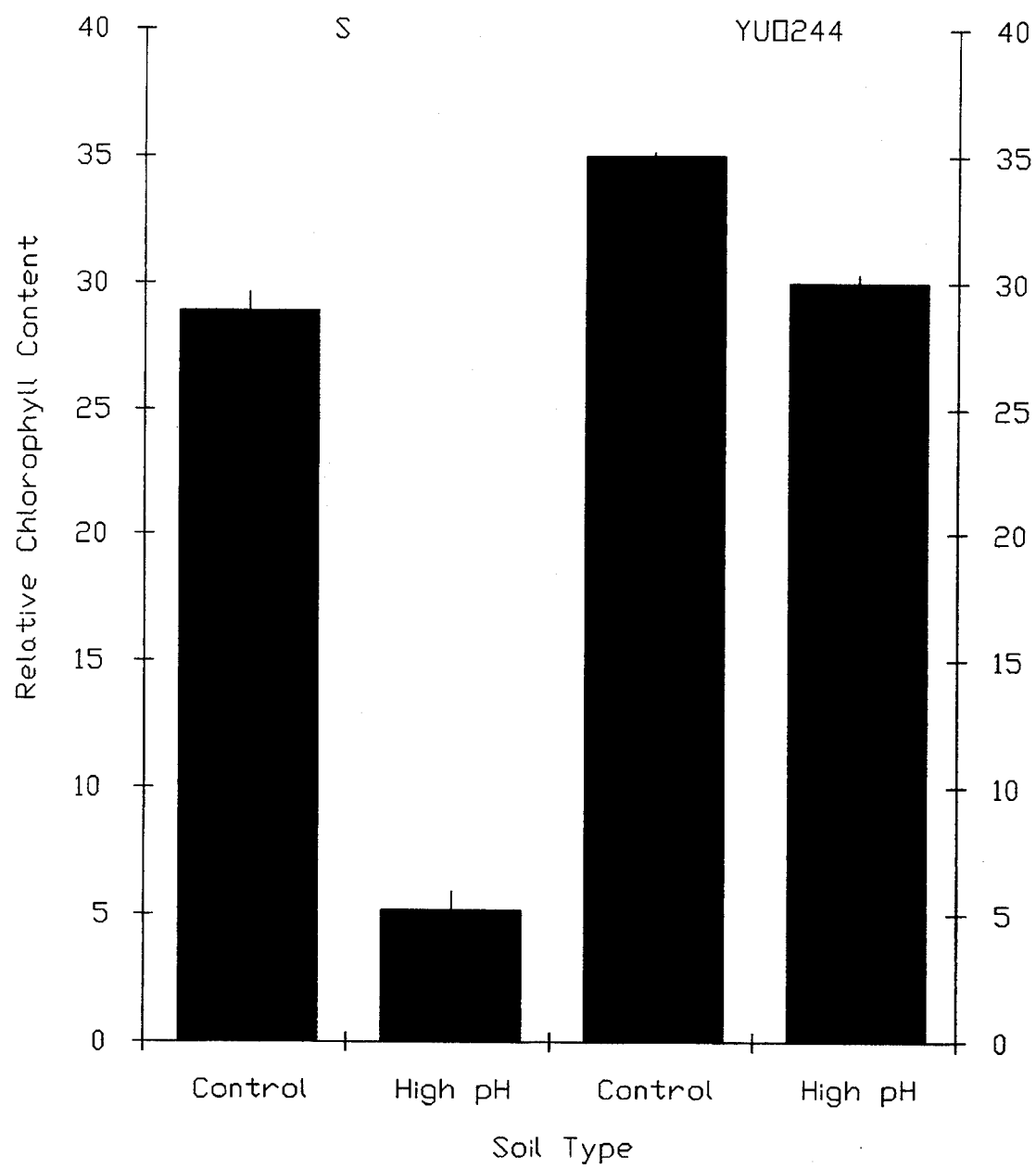
FIG. 3 shows a controlled environment comparison of the RCC of tolerant(donor) line and a sensitive (recipient) line growing in HpH conditions (~pH 8.5) and optimal pH conditions (pH 6.8)

Measurements of RCC were taken on 195 inbred lines each with two replicated single row plots. The mean RCC value for each inbred line is presented in FIG. 2. As can be seen from the data presented in FIG. 2, a large genotypic range in tolerance/sensitivity exists within the lines studied. The range of RCC values runs from 11.18 at the sensitive end, up to 52.08 at the tolerant end. The tolerant donor line (YU0244) was included in the screen, and demonstrated a significantly higher level of tolerance than any other line tested. The RCC value for YU0244 was 52.08. A comparison between the RCC content of the inbred in which the trait was to be introgressed S and the donor YU0244 R is shown in FIG. 3. FIG. 3 shows the RCC of S in good soil and the RCC of S in HpH soil, likewise the RCC of YU0244 is shown in both soils. Clearly S has a loss of RCC in HpH soil in comparison YU0244 shows only a small decrease in RCC in HpH soil. In fact YU0244's RCC in HpH soil is similar to S;s RCC in good soil. This invention allows the selective introgression into S of the exogenous chromosomal regions of YU0244 which give the HpH tolerance trait, while permitting the majority of the S background to remain in the converted line.

Figure 4:
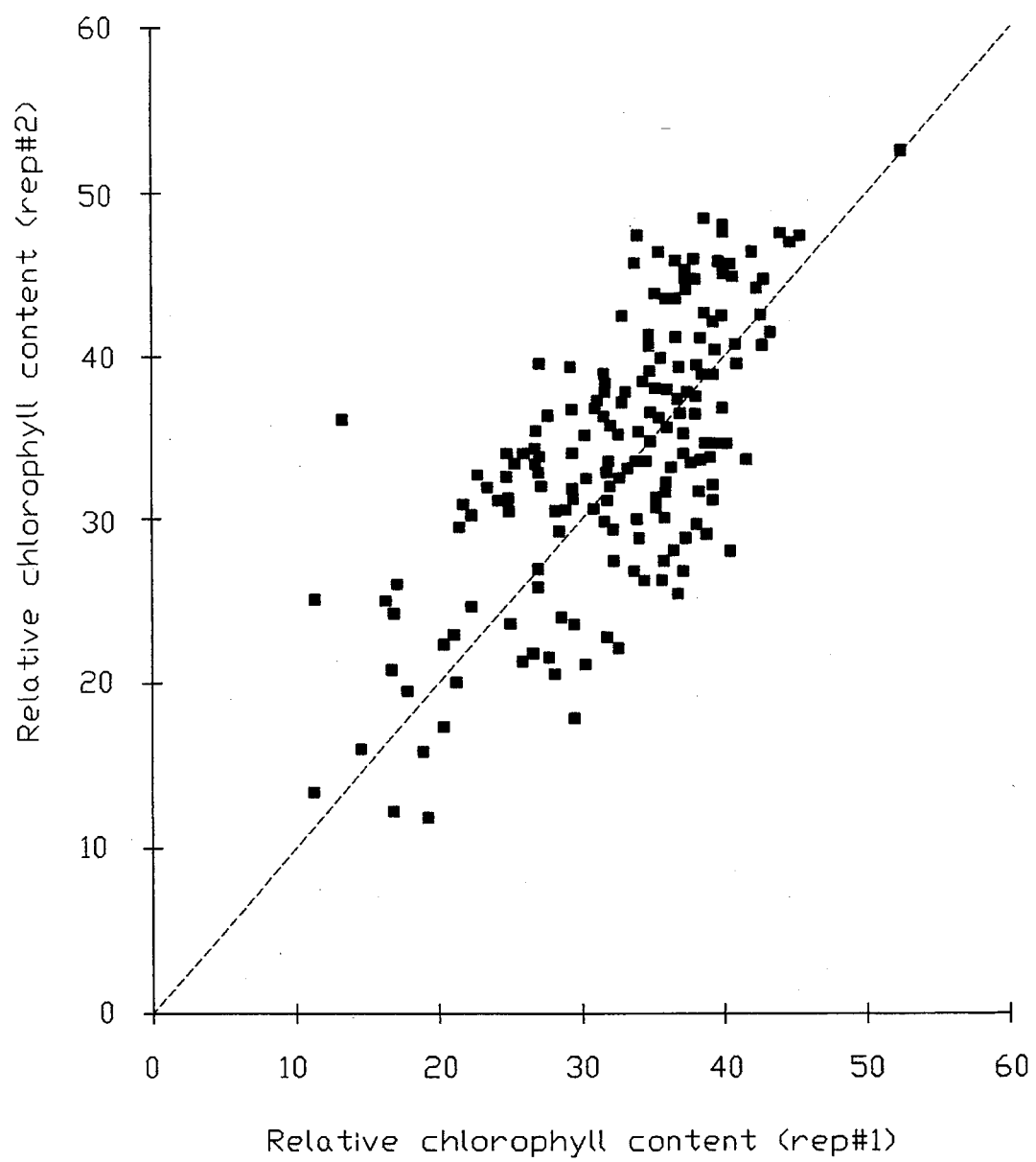
FIG. 4 shows the relationship of the RCC scores of two replicates of 188 inbreds grown in a high pH location Nebraska demonstrating genetic variation for the HpH trait.

The relationship between RCC values in rep 1 and rep 2 for each inbred line is presented in FIG. 4. As can be seen, there were differences in relative RCC value between inbred lines in reps 1 and 2, which would be expected. However, a clear positive relationship exists in RCC values between reps 1 and 2.

Figure 5:
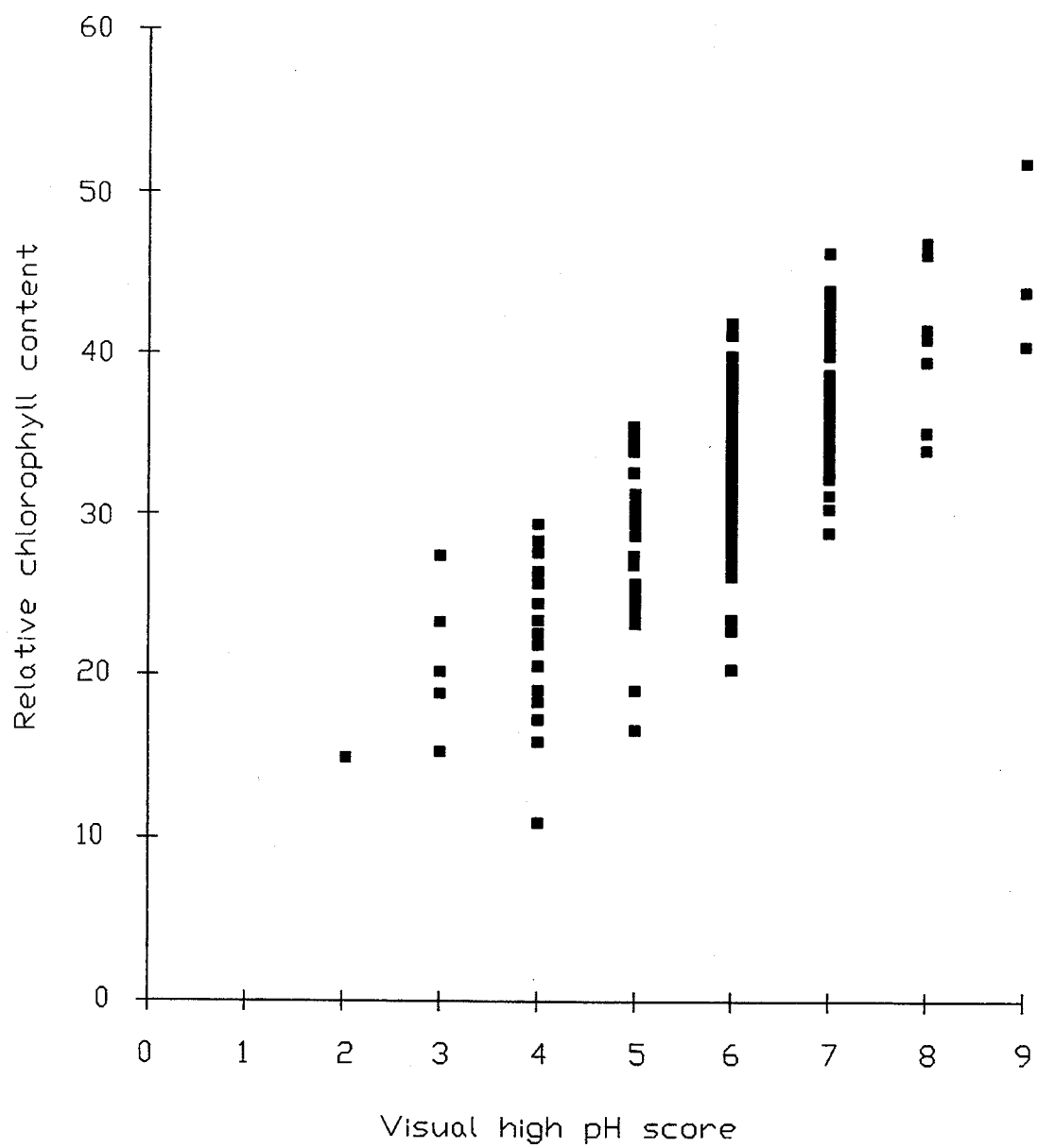
FIG. 5 shows the relationship between RCC and visual high pH score of the 195 inbreds grown at a high pH location in Nebraska in FIG. 2.

In order to confirm that there is a relationship between visual score and measurements of RCC, we made a comparison between the two measurements. The data presented in FIG. 5 shows the relationship between the two scoring methods. From the data presented in FIG. 5, a range of RCC values fall within each of the visual classes. The RCC value is far less subjective than a visual score and is therefore more capable of quantifying finer differences between lines.

Figure 6:
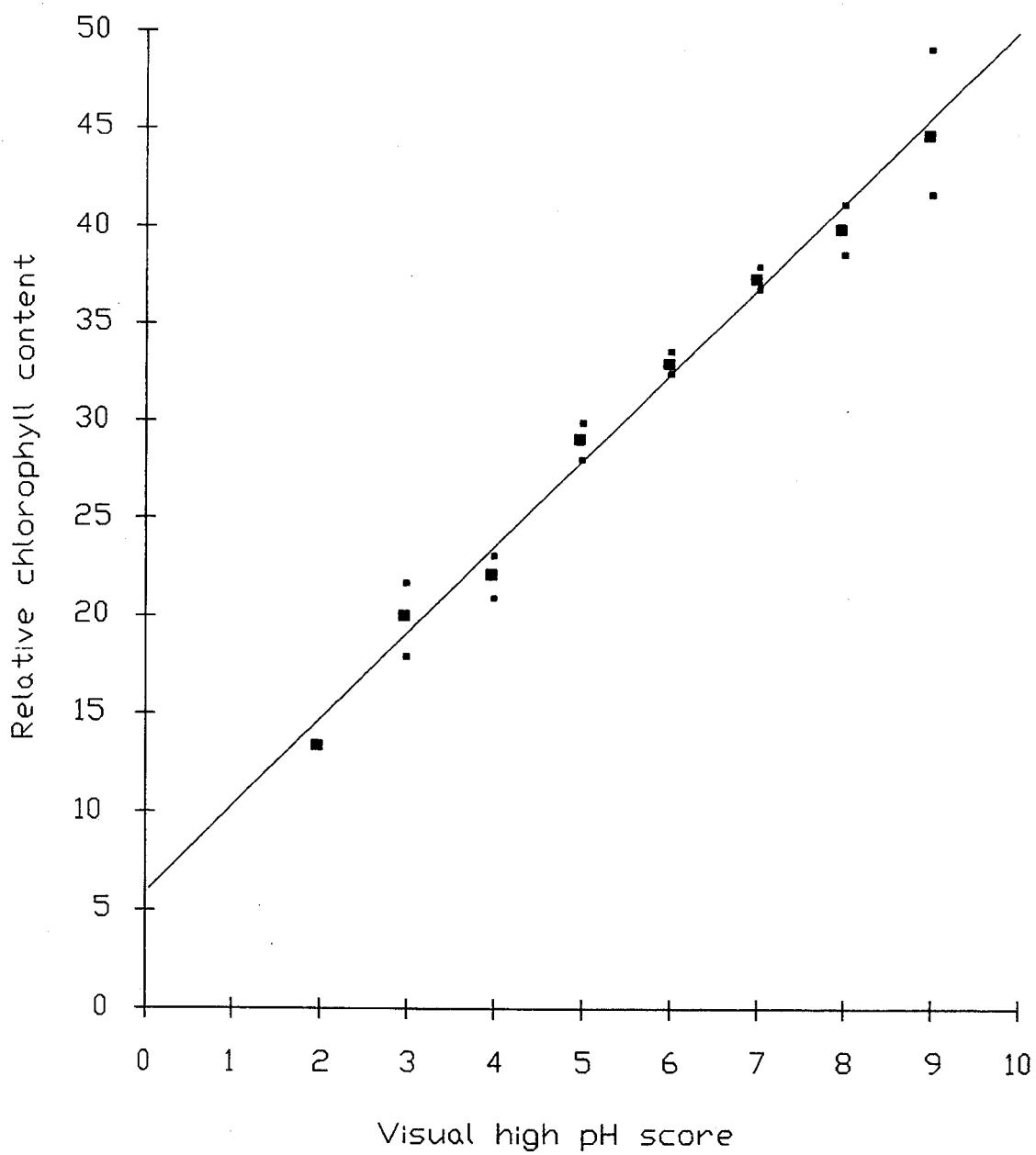
FIG. 6 shows the relationship between the mean RCC and the visual high pH score (best fit line)

A plot of the mean of the RCC values within each of the visual classes, gives a clear positive relationship presented in FIG. 6. The data presented in FIG. 6 clearly states that the two measurements are closely correlated and that one is a useful prediction of the other. While a visual assessment is quite adequate for classing fixed lines or hybrids, measurement of RCC is clearly more accurate in quantifying different levels of tolerance/sensitivity in segregating populations. Furthermore, combining the more objective RCC measurement with RFLP's provided a more accurate method for identifying the location and gene action of the high pH tolerance gene(s).

The soil in Colorado, near Yuma and the soil in Nebraska near Morrill in which the HpH testing of the inbreds was performed is known to be HpH soil of the calcareous type. This soil evidences the white dirt characteristic associated with calcareous soil. It is known in the industry that HpH soil has detrimental effects on the hybrids yield potential as was clearly evidenced in FIG. 1. The inbred line YU0244 was developed by ICI SEEDS a the Yuma Breeding station. The genetic background demonstrates a high degree of tolerance to high pH soils, a rating of 8 on a 1–9 scale, where 1 is highly sensitive and 9 is highly tolerant. In contrast the "S" (sensitive) lines into which the tolerance was introgressed demonstrated a high degree of sensitivity to high pH soils were a rating of 2–3. Likewise the "S" line used for identification of the chromosomal regions of interest rated 2–3. The attempt by the breeders to convert the "S" lines to HpH tolerance by traditional breeding techniques was unsuccessful. There was a loss in the tolerance level in the traditionally developed inbreds which used YU0244 as a donor parent for the allele having HpH tolerance. Thus a group of inbreds which were rated at 2–3 were used in the development of the present invention.

These screening procedures (visual and RCC) allowed the identification of the extreme tails of the "R"×"S" $F_2$ populations. In other words, plants which were extremely susceptible and plants which were extremely resistant to HpH were identified.

Figure 7:
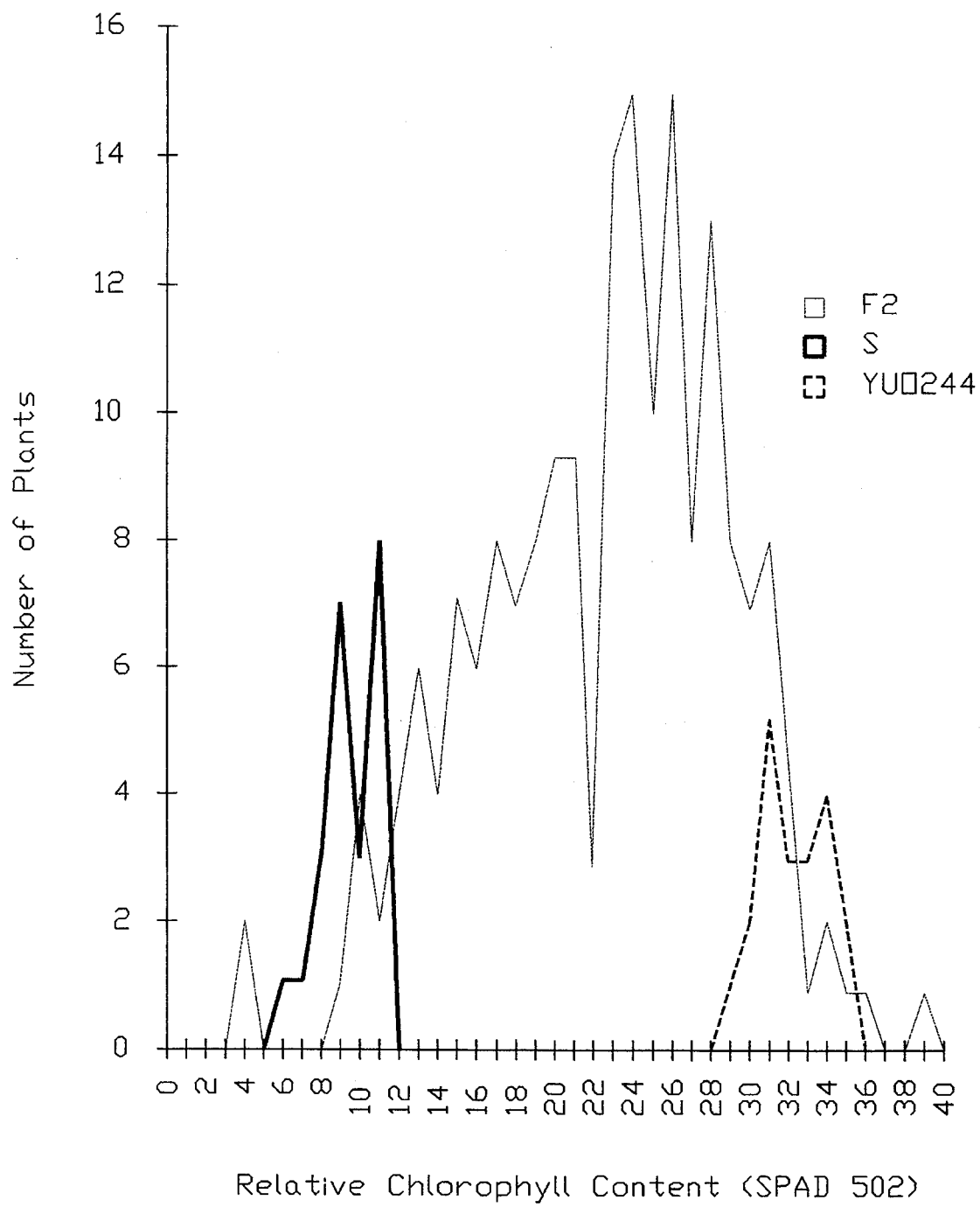
FIG. 7 shows the RCC measured in $F_2$ population of YU0244/S and the RCC measured in "S" and in YU0244.

FIG. 7 shows the frequency distribution of the $F_2$ plants in the controlled environment screen, in relation to the two parents, YU0244 and "S". During the course of the screen, all the plants were fed with $KNO_3$ as a source of nitrogen. All the other essential nutrients were present in the Yuma soil, and had been previously checked with a thorough soil test. As can be seen from the data presented in FIG. 7, there was a large genotypic range in response from the $F_2$ plants. RFLP linkage analysis which confirms that there are in fact 3 major genes (two additive to dominant, one recessive) and a minor gene with a dominant gene action. Surprisingly,one of the genes maps to the same location as ys3 which is a known mutation site for delinquent iron ($Fe^{3+}$) metabolism in corn. This finding is highly significant in itself, and supports the hypothesis that a deficiency in iron metabolism is the underlying cause of the high pH sensitive response. The precise chromosomal location of the tolerance genes is detailed in the map in FIG. 11.

Figure 8:
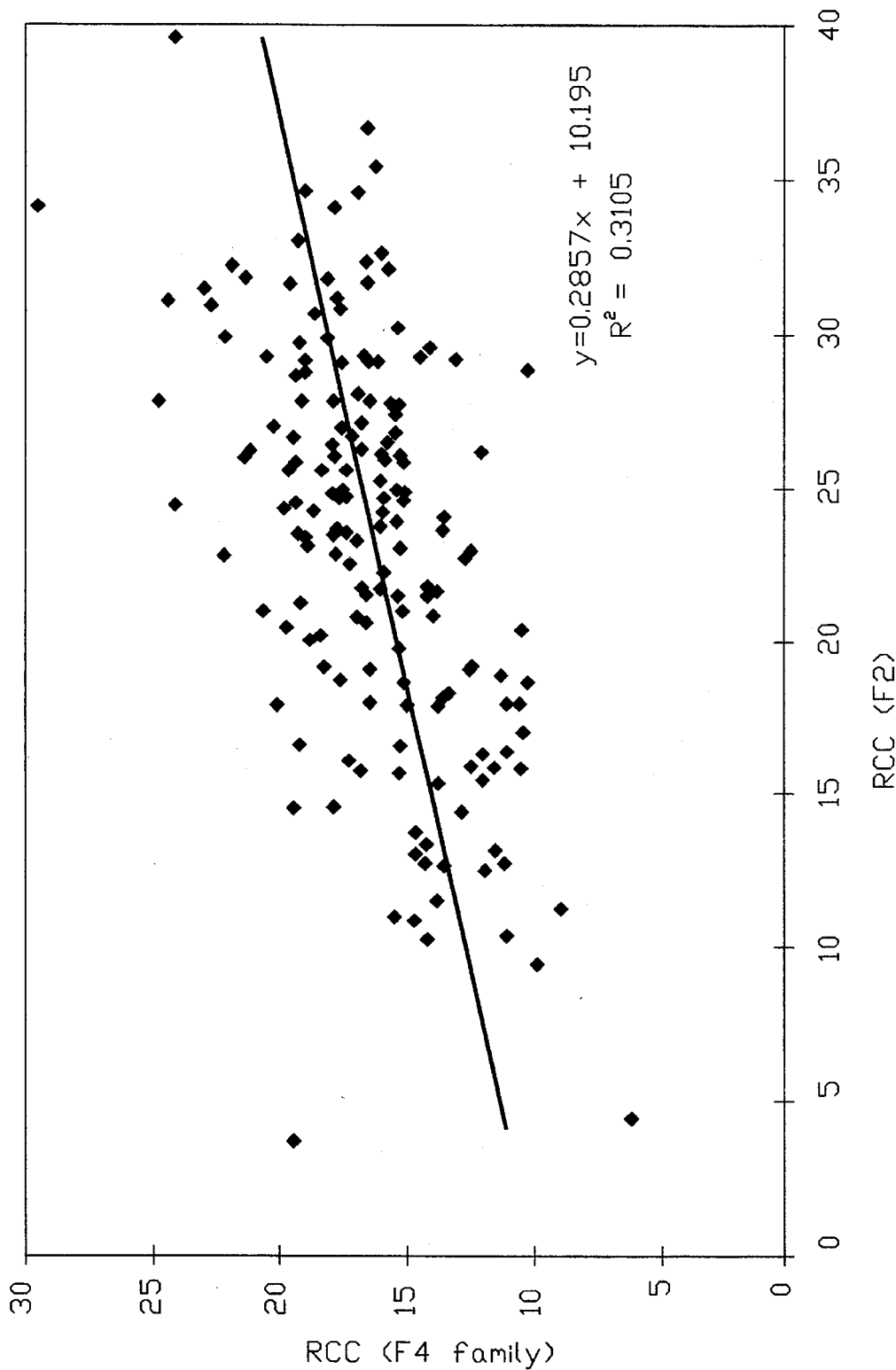
FIG. 8 shows the relationship between RCC data from individual $F_2$ plants of YU0244/S and their subsequent $F_2$ derived $F_4$ families in a controlled environment HpH screen.
Figure 9:
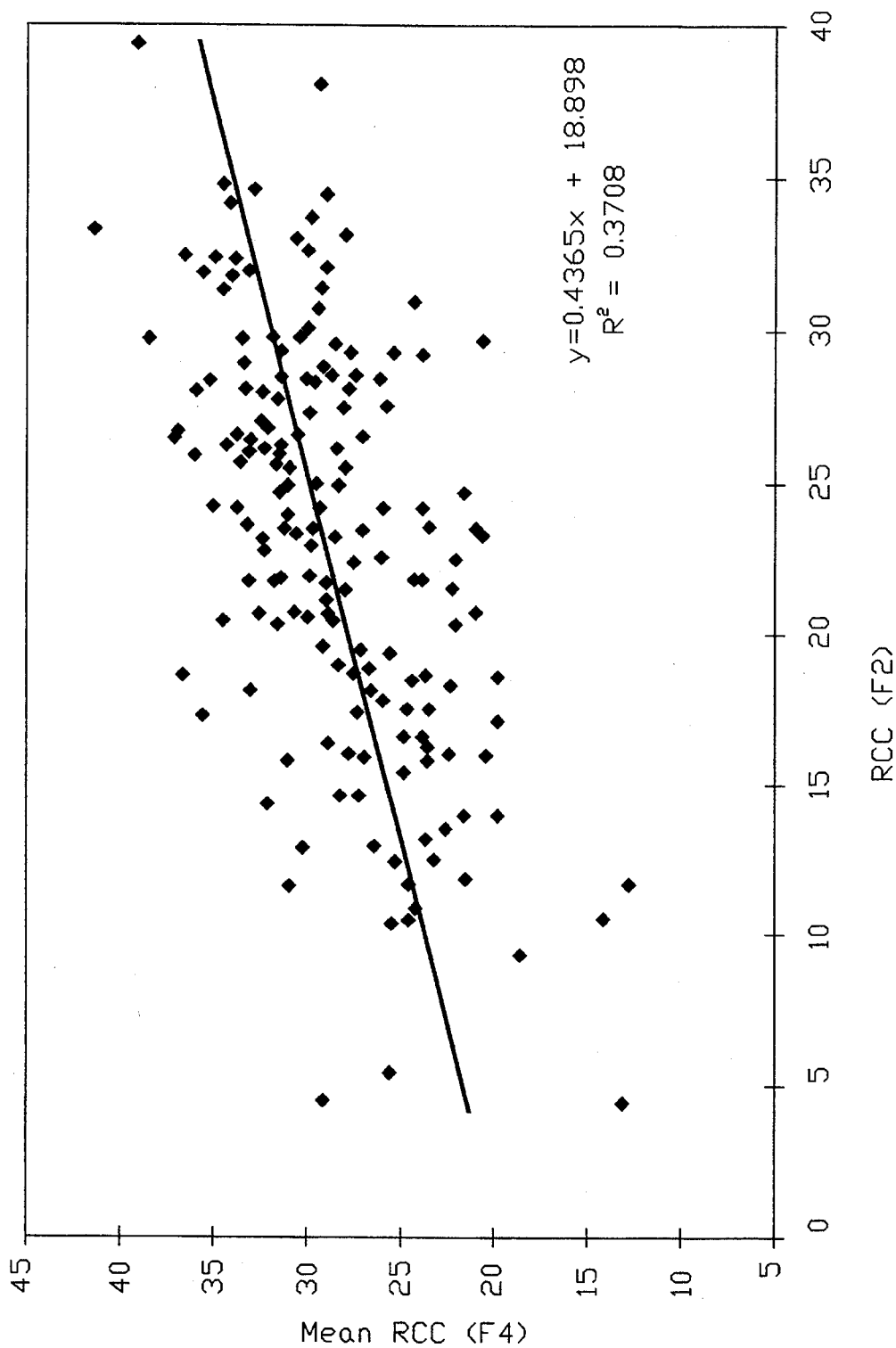
FIG. 9 shows the relationship between RCC data of F2 plants and the RCC of the $F_4$ families in the field locations in Colorado and Nebraska.
Figure 14A:
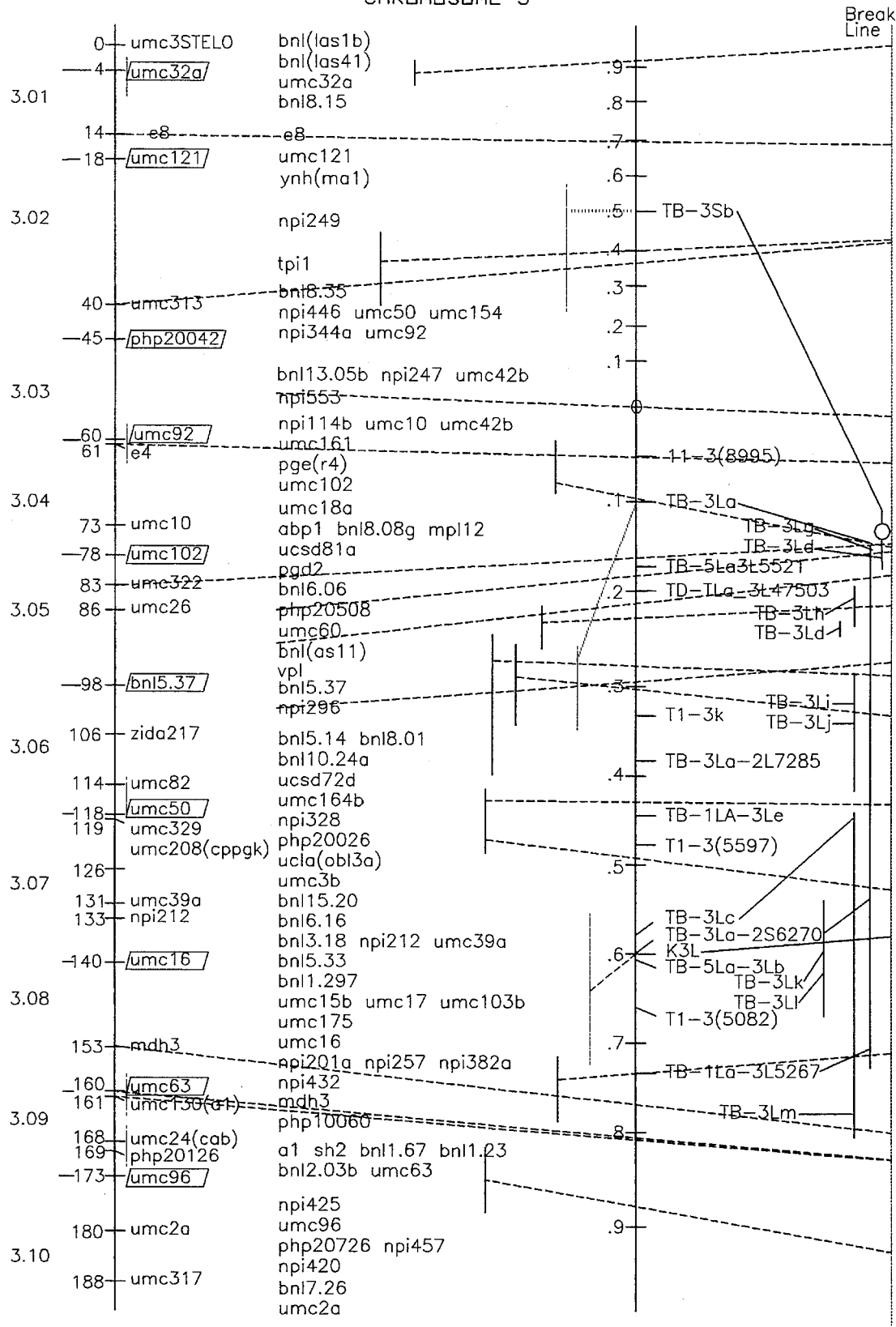
Figure 14B:
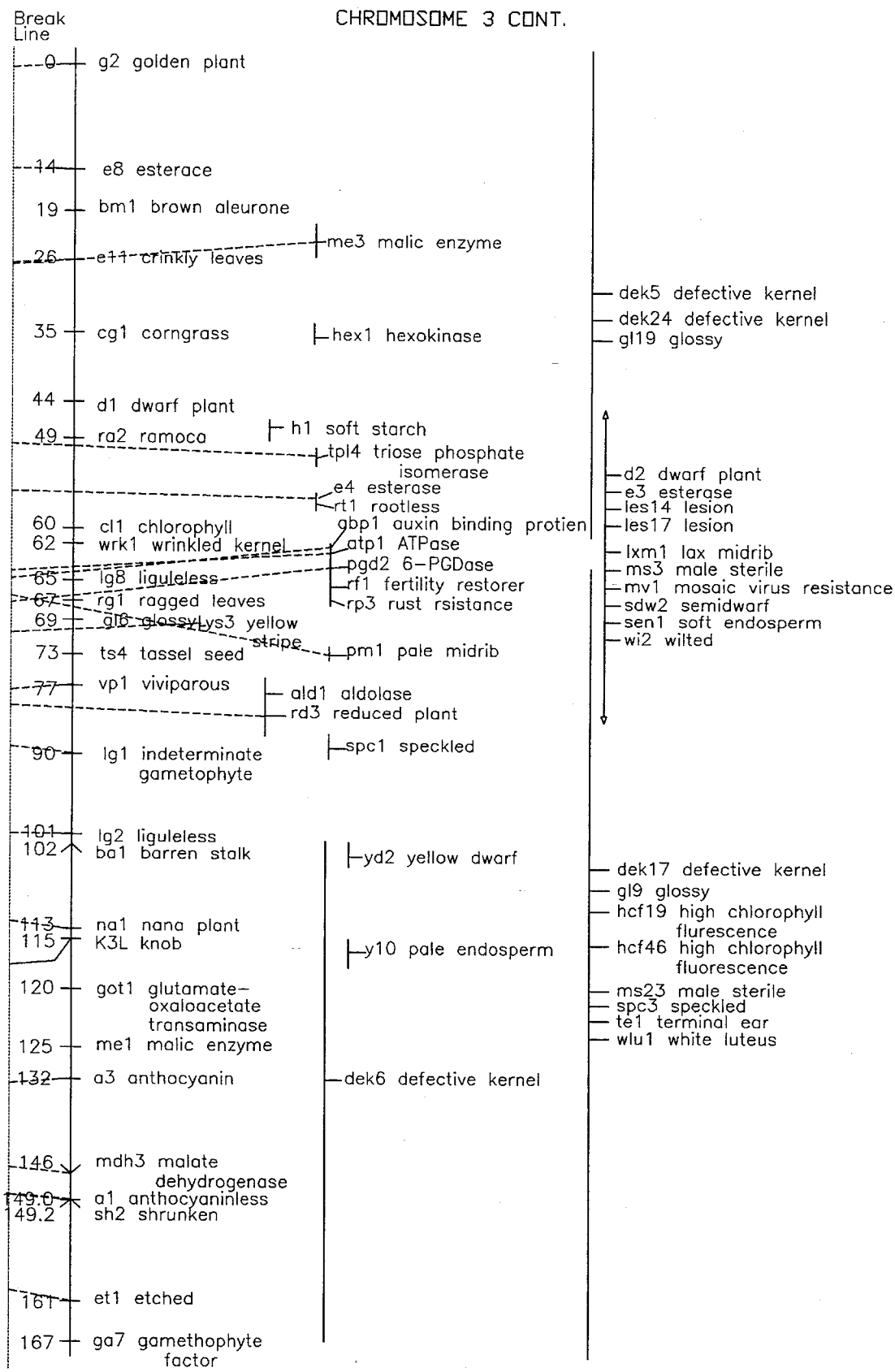
Figure 14C:
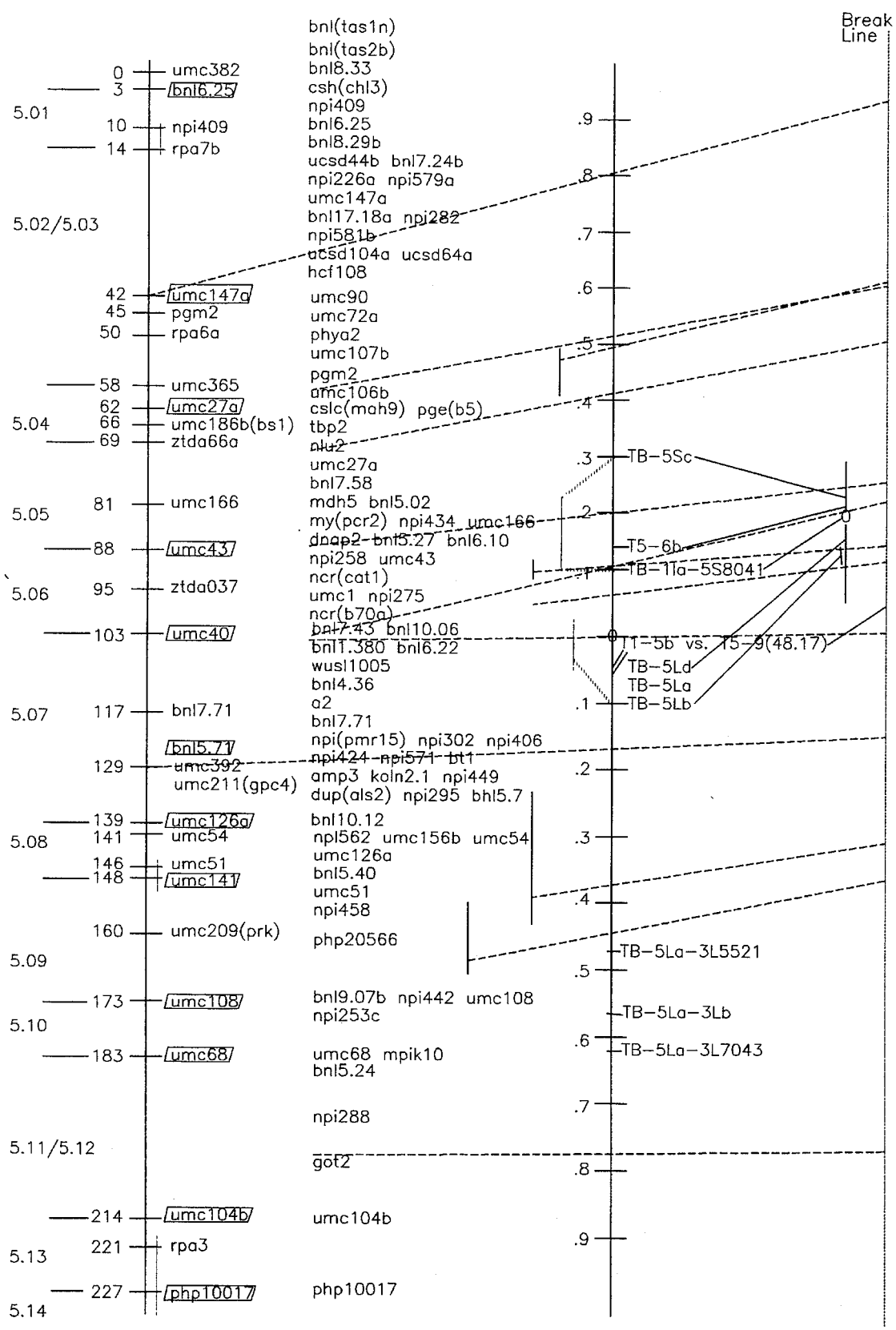
Figure 14D:
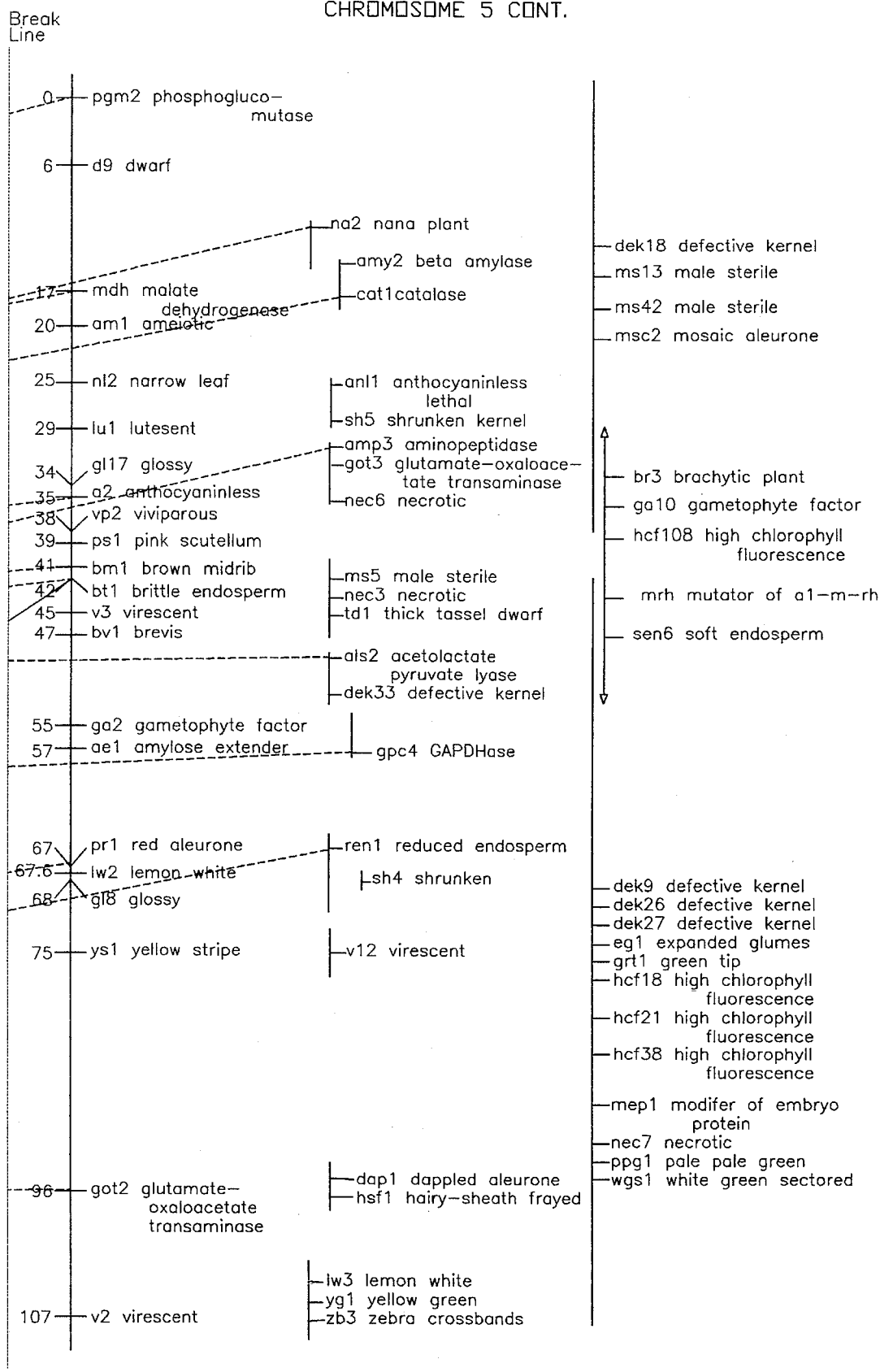
Figure 14E:
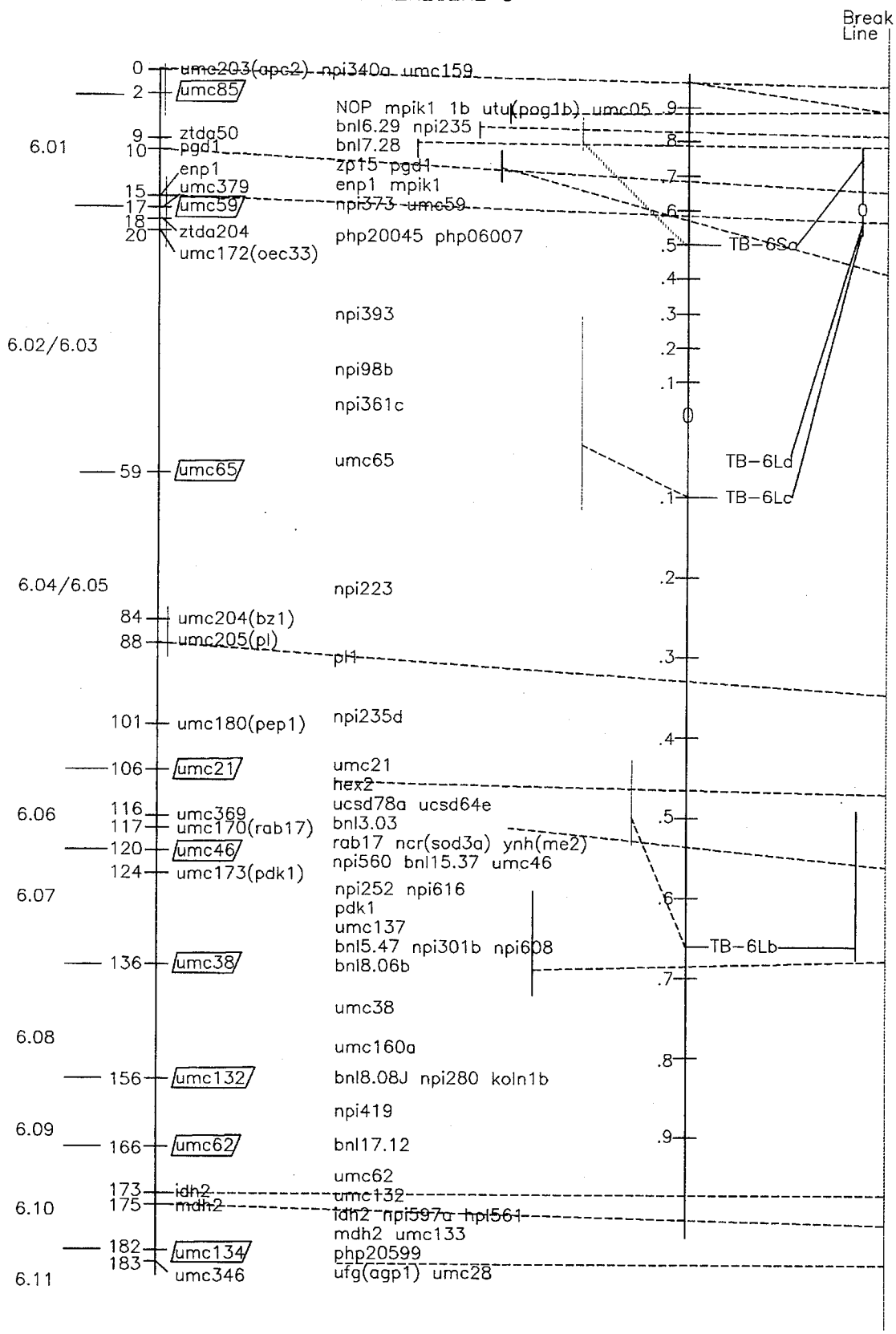
Figure 14F:
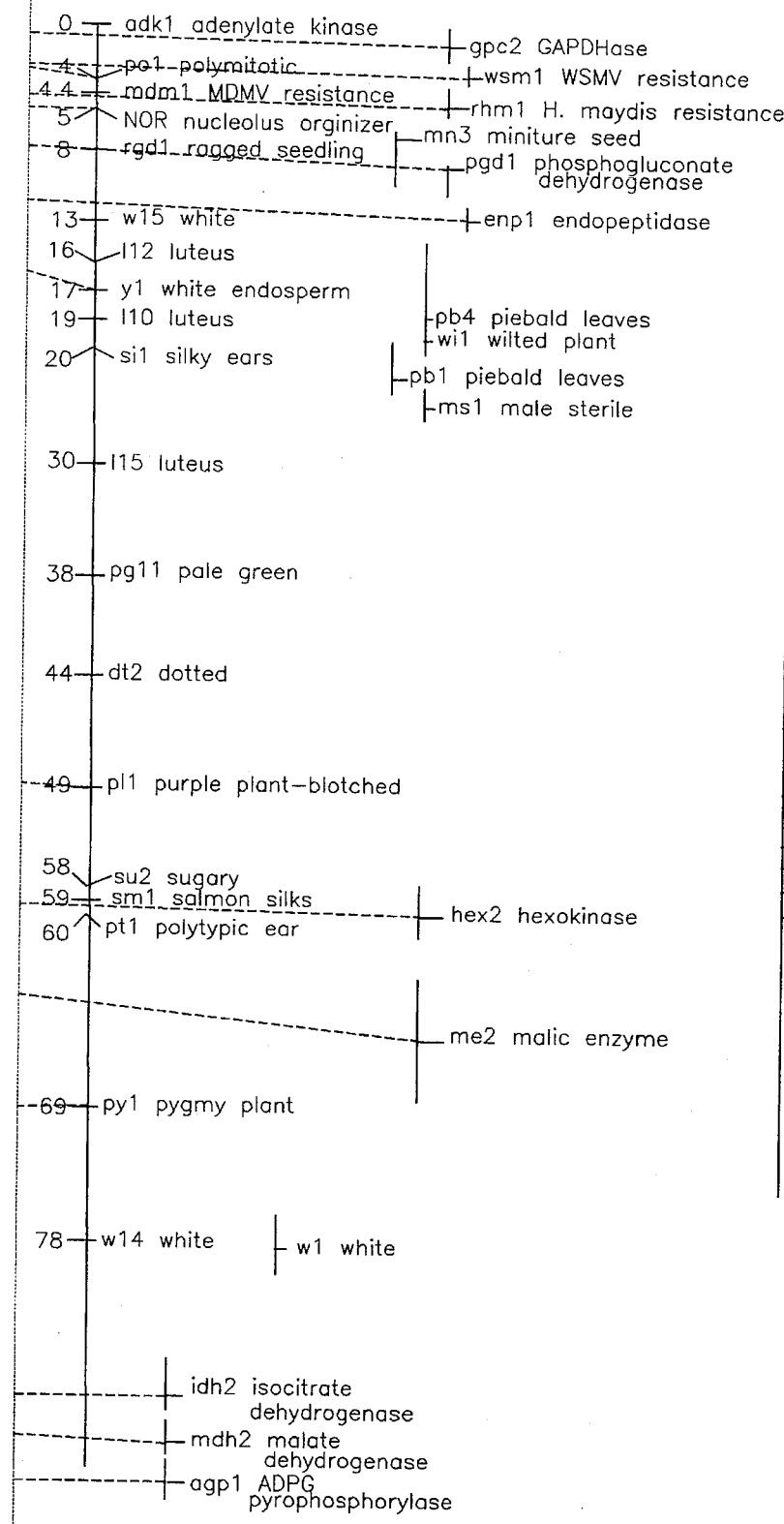

FIG. 8 shows the correlation of the mean of RCC of $F_4$ families with the RCC levels of the parent of $F_2$ plants. Both of these RCC were developed by lab screens. The correlation shows that the RCC level is being carried into the $F_4$ families fairly consistently. FIG. 9 shows the correlation between the RCC values of the $F_2$ plants produced in controlled laboratory conditions and the RCC values of the $F_4$ families grown in the field conditions. Again, the correlation shows that the tolerance trait is being passed to the $F_4$ families and the trait is expressing in field conditions.

The data in FIG. 10 shows the tolerance levels by RCC of the $F_4$ family members. The sensitive check had a RCC of 14.85 in Gering and 11.25 in Yuma. The Yuma pH soil levels are higher than the pH levels of the Gering soil. Both the tolerant check and the sensitive check had higher RCC levels in the Gering soil than the Yuma soil as was predicted by the scientists. Clearly in the $F_4$ families, the trait is still segregating as expected. This segregation results in a bell curve of tolerance with most of the population being in the 20–30 RCC range. The extremely high RCC plants were selected and RFLP analysis run on them to determine the homozygosity for the desired plants.

Then identification of the chromosomal regions associated with tolerance to HpH soil were located by the use of comparison of the RFLP data between the susceptible and resistant plants with the screening results. Approximately 150–200 plants were used to generate the data shown in FIG. 8. The RFLP data shown in FIG. 8 was generated by the following RFLP protocol:

A. DNA Extraction

The corn plant tissue was lyophilized, ground to a fine powder in a mill and the DNA was extracted. 100 ml of RNase (10 mg/ml) were placed in tubes and the supernate was filtered and placed in the tubes and incubated. The DNA precipitate was snagged, transferred to a culture containing 76% ETOH/10 mM $NH_4Ac$, and incubated. See Proc. Natl. Ac. Sci. USA 81:8014–8018.

B. DNA Digestion

The DNA was quantified fluorimetrically, and digested to completion. DNA was loaded onto slab gel and electrophoresised. DNA was transferred onto Hybor-N+membrane (Amersham) via southern blotting. The protocol used is the protocol suggested by the manufacturer.

C. Southern Blotting

A matrix of Hybond $N^+$ Nucleic Acid transfer membrane, was soaked in 25 mM $NaH_2PO_4$ at –pH 6.5. The blots were baked for two hours. The Southern Blot procedure is well known in the art at J. Mol. Biol. 98:503 (1975).

D. Oligo Reaction 40 mg DNA was mixed with sufficient $H_2O$ to make up 3 ml of solution. The DNA was denatured for ten minutes at 95° C. and then 10 ml oligo buffer, 2 ml BSA, 5 ml 32P-dctp, 2 ml Klenow was added. The sample was incubated and then a 150 ml stop buffer was added.

This protocol is published in Feinberg, A. P., B. Volgelstein, Anal. Biochem. 132:6, 1983.

E. Probe Hybridization

Probe fragments were generated from recombinant plasmids using PCR and the products gel-purified prior to labelling with 32p-ctp (Amersham) via random priming. The blots were decanted and placed on Kodak XAR X-ray film and exposed. The procedure used is published in B. Buddowle, et. al. Crime Laboratory Digest 15:3–21, 1988.

F. Probe Removal

The blots were washed in 5 mM Tris-HCL/pH 8.0, 0.2 mM EDTA 0.05% pyrophosphate, 0.1x Denhart's for 1–2 hours at 65°–75° C. Denhart's Solution—50x is formed as follows: Ficol—5 g, polyvinylpyrolidone—5 g, BSA (Pentax Fraction V)—5 g, $H_2O$—500 ml. Then rinsed in 1xSSPE. SSPE (2xx) is formed as follows: 174 g NaCl, 27.6 g $NaH_2PO_4$ $H_2$), 7.4 g EDTA, 800 ml $H_2O$, adjust pH 7.4, bring volume to 1 liter.

Two methods of statistical analysis were done with the data resulting from the above procedure, a locus-by-locus analysis of variance and an analysis using pairs of RFLP markers. The Statistical Analysis System (SAS) package of programs was used for data analyses. SAS is commercially available from: SAS Institute, Inc., SAS Campus Drive, Cary, N.C. 27513. The GLM procedure on SAS was run, by RFLP locus, for the means of three allelic classes: SS, SR, and RR, designating homozygous RFLP marker alleles for one parent, heterozygous, and homozygous for the other parent. This analysis gives a probability of observing differences in average values for each of the three classes by chance, called the level of significance. In keeping with general scientific usage, significance levels less than 0.05 are denoted "statistically significant," and those less than 0.01 "highly significant," both indicating that the class averages are enough different to be unlikely to have arisen by chance.

The plant source of the genetic material associated with the listed probes is indicated in FIG. 8. Negative signs indicate the source of resistance is the susceptible parent, no sign (i.e. positive) indicates the source is the resistant parent.

Rsq.=estimated proportion of total variation associated with the RFLP probe based on the difference between rated symptoms of the homozygous resistant and homozygous susceptible allele class.

PR>F=probability of chance occurrence.

FALC A=estimate of half the difference in true homozygous class means, Falconer's 'a'.

The probes are listed by their first letter and their number, i.e. probe on BNL7.25 (as listed on FIG. 14) would be listed on FIGS. 12 & 13 as BO725. The large numbers bolded under the heading "Sum" indicate the statistically significant associations between the trait and the chromosomal region associated with the corresponding RFLP probe. FIG. 13 shows selected probes by which the genetic material evidenced tolerant HpH response in the RR plant (genetic information for the probe indicates derivation from the resistant (YU0244) plant). Results of the statistical analysis of the plant's RCC rating at each probe location based on the level of statistical significance, identified the chromosomal regions of interest.

Three major effects were observed from YU0244 on chromosome three center-long (HpH2); chromosome 3 center-short (HpH1), and on chromosome five long (HpH3). The gene action of the regions on chromosome three are additive to dominant and the gene action of the region on chromosome five is recessive. The fourth chromosome region on 6 center (HpH4) also gave a significant association with high pH tolerance coming from YU0244. The effect of this region 6 on the tolerance is less than the chromosome regions HpH1 and HpH$_2$ and HpH3 on chromosomes three and five. The gene action of HpH4 is dominant.

Linkage block one, locus 1, is the genetic material located between Map Unit 61 and Map Unit 83 proximate probes BNL8.35–UMC102 on chromosome three.

Linkage block two, locus 2, is the genetic material located between map unit 98 and map unit 106 proximate probes BNL5:37–UMC60 on chromosome 3.

Linkage block three, locus 3, is the genetic material located between Map Unit 95 and Map Unit 103 proximate probes BNL7.71, UMC68 on chromosome 5.

Linkage block four, locus 4, is the genetic material located between Map Unit 9 and Map Unit 20 proximate flanking probes UMC85–UMC59 possibly between probes BNL6.29 and UMC59 on chromosome 6.

It is emphasized that this invention may be practiced using any molecular markers which map in the regions of the map at the locations indicated, provided that the markers are polymorphic for the cross.

The elite donor parent YU0244 carries significantly desirable agronomic characteristics. Thus it was not necessary to identify the chromosomal regions of interest as closely as possible because introgressing additional material with the linkage blocks 1–4 into elite germplasm, should only carry desired traits along with the tolerance to HpH into the genome of the resultant inbred and likewise hybrid combination. Thus to generate a commercially viable inbred, the beginning crossover event (the crossover closest to the distal end of the short arm of the respective chromosome) and the ending crossover event (the crossover closest to the distal end of the long arm of the respective chromosome) can occur without strict precision and accuracy because carrying excessive genetic material from YU0244 into the resultant inbred should not be detrimental. However, precision and accuracy can be necessary and useful if the desired inbred is developed to have the background of a sensitive plant and only the HpH exogenous material at HpH1–4 giving HpH tolerance at the loci 1–4.

It should be readily understood in the art that the other probes which more closely map the linkage blocks as identified by the map units could be employed to identify the crossover events. The linkage blocks listed permit the tolerance trait to be readily identified and introgressed into other germplasm material. Larger linkage blocks could likewise be transferred within the scope of this invention as long as the material introgressed is sufficiently tailored to avoid transfer of wanted traits into the resultant plant. It will be appreciated that breeding efforts which seek to improve agronomic traits while attaining HpH tolerance are empowered by the arrangement of the superior allele in these linkage blocks.

Chromosome region one (on chromosome three) is the genetic material expressing the desired trait between flanking probes BNL8:35 and UMC102.

Chromosome region two (on chromosome three) is the genetic material expressing the desired trait between flanking probes UMC60–BNL5:37.

Chromosome region three (on chromosome five) is the genetic material expressing the desired trait between flanking probes BNL7.71–BNL5.71.

Chromosome region four (on chromosome six) is the genetic material expressing the desired trait between flanking probes BNL6.29–UMC172.

Once the chromosomal regions associated with the tolerance to HpH were identified, the regions could be precisely and accurately introgressed from the HpH resistant donor into an elite inbred which has desirable agronomic traits. The trait was then introgressed "cleanly" from one elite inbred into another elite inbred. Ultimately, a resultant hybrid which has tolerance to HpH is produced. The chromosome regions 1–4 or some of the chromosome regions formed of YU0244 genome or progeny of YU0244 genome which is exogenus to the genome of the rest of the plant. It should be understood that a variety of hybrids with this trait could be developed and seed therefore produced and sold to farmers for maize production in HpH prone areas as well as in other locations.

As stated herein, the objective of this invention is to improve the resistance to HpH of elite breeding lines without substantially affecting their combining ability. The term "elite" is a term of the art and its meaning is well known.

Many factors contribute to the elite nature of these breeding lines but of these factors the yield, in hybrid combination, and the moisture content of the seed, percentages of root and stalk lodging are important. In performing this invention, then, the introgression of the tolerance trait can be monitored from generation to generation and, the progressive restoration of the genetic background of the non donor parent may also be observed. The best selections made by using RFLP fingerprinting ultimately require field testing in HpH soil so that the tolerance trait is confirmed as is the yield of the newly tolerant line. Ideally, the product line should have the same combining ability and substantially the same yield in high pH soil or good soil as its elite HpH sensitive parent or its resistant parent.

The principal feature of this invention is the transfer of genes from a relatively resistant donor to a relatively susceptible recipient. However, the level of tolerance recipient lines is, of course, relative to the soil type, and the sensitive recipient may itself possess tolerance genes which may usefully be retained in the genome of the improved lines.

By virtue of this invention it is now possible to use molecular markers to introgress the HpH trait from YU0244, or from sibling, or progeny thereof, into elite but susceptible lines. The following example outlines the introgression of the identified linkage block into an inbred designated ZS269. ZS269 is a yellow dent corn. The introgression of the desired linkage blocks in an elite inbred resulted in an improved inbred designated ZS269:HpH.

The original $F_3$ families (YU0244×ZS269) were increased (sibmated) in an early Hawaii nursery (making $F_4$'s), and immediately turned around in Hawaii to make the $F_5$ families. The $F_4$'s were also test crossed to an elite inbred (making a hybrid suitable for the season length in the Western upper corn belt).

The 175 $F_4$ families were tested at five high pH locations. The high pH locations are as follows:

| | |
|---|---|
| Most severe: | YUMA |
| | GERING |
| | AULT |
| | BAYARD |
| Least severe: | MORRILL |

Of the five locations, three were chosen for measurement of tolerance/sensitivity by measuring relative chlorophyll content (RCC). Each entry was planted in single row plots with 2 reps per location.

With regard to the 175 families crossed to the elite inbred, the hybrids were planted in two row plots with one rep per location. A total of six locations were planted, three of which were high pH locations, Yuma, Bayard and Morrill, and three of which are high yielding locations, LeSalle, Johnstown and Paxton. Two check hybrids were planted. Approximately 50 of the 175 $F_4$ families were test crossed to a different elite inbred, and these were tested independently of the other crosses.

The result of the various test crosses was as expected, the gene locations were correct and the tolerance level to HpH was reduced if the four gene locations (or at least the two primary gene locations) were not homozygous in both sides of the cross. The inbreds were substantially more tolerant to HpH even though all four regions were not fixed in every inbred.

The following is a protocol for developing an inbred having the desired trait using traditional breeding selection in combination with RFLP Data: on the homozygosity of the trait; and the similarity of the RFLP data to the RFLP data of parent of choice. BC1 means back cross one, BC1S1 means the backcross has been selfed once.

BC1 screen: Screen 400–500 BC1 seedlings in controlled environment. Based on RCC data, select top 100–120 seedlings and transplant to greenhouse. RFLP screen on 100–120 BC1 selections to identify the 50–60 individuals with all four HpH genes (one of the major genes is recessive). The 50–60 individuals would be screened for background genotype in order to select the best individuals for backcrossing. Two or more can be selected. All 50–60 individuals would be selfed and form BC1S1 families.

BC2 screen: 200–250k from each of the selected two BC2 ears screened in controlled environment. Select top 100–120 seedlings for transplant to the greenhouse. RFLP screen to identify 50–60 plants with all four genes. Background genotype screened and two or more individuals selected to self and backcross.

BC3 screen : Use the yield data from the $F_4$ families with hybrids and identify any potential yield/agronomic conflicts around the four HpH genes. 200–250k from each of two BC3 ears screened in controlled environment. Select top 100–120 seedlings for transplant to the greenhouse. RFLP screen to identify 50–60 plants with all four genes. Background genotype screened and two or more plants should be selected for selfing and backcross.

BC3S1 screen: Screen up to 250k from each of two selected BC3 selfed ears (BC3S1 seed). Select 20–30 seedlings with high RCC values, of which 8–10 will be fixed at all four HpH loci. The 8–10 fixed individuals will be identified using RFLP's and selfed. BC3S2 seed will have a progeny test.

BC3S2 seed:
Test cross to second inbred made by the process listed above. If necessary a BC4 can be made and BC4S2 seed can be further increased and test crossed.

It would achieve the greatest HpH resistance in the resultant plant if both male and female inbreds were fixed for all four gene locations. But at least having the recessive gene action fixed in both parents. Additionally fixing of the additive-dominant gene action is also preferable.

This invention provides a repeatable method of obtaining HpH tolerant inbred lines having the elite characteristics and the HpH tolerance which can be employed to produce commercially acceptable HpH tolerant hybrids.

Although the foregoing invention has been described in some detail by way of illustration and example for purposes of clarity and understanding, it will be obvious that certain changes and modifications may be practiced within the scope of the invention.

We claim:

1. An elite inbred maize plant and parts thereof comprising a genome, homozygous with respect to genetic alleles which are non-native to a first parent of said elite inbred and native to a second parent of said elite inbred, said second parent line selected from the group consisting of maize inbred YU0244 having ATCC Accession No. 75869, tolerant progeny and tolerant hybrids thereof, wherein said elite inbred maize line exhibits tolerance to high soil pH as measured by relative chlorophyll content of the plant.

2. A maize plant having high pH soil tolerance, the genome of which contains genes associated with said high pH soil tolerance at at least one of the loci selected from the group consisting of:

(locus 1) chromosome 3, proximate map unit 61–83;

(locus 2) chromosome 3, proximate map unit 98–156.

(locus 3) chromosome 5, proximate map unit 95 and map unit 103;

(locus 4) chromosome 6, proximate the map unit 9 and map unit 20;

references to map units being references to the maize chromosome map FIG. 14.

3. A plant as claimed in claim 2, which is homozygous at each of the loci numbered 1 to 4 specified in claim 2.

4. A plant as claimed in claim 2, in which the donor tolerant parent is selected from the group consisting of the corn line designated YU0244 having ATCC Accession No. 75869, tolerant progeny thereof and tolerant hybrids thereof.

5. An inbred maize line, designated YU0244, having improved tolerance to high pH soil, seed of which has been deposited at ATCC under the terms of the Budapest Treaty, on Aug. 22, 1994, Accession Number 75869.

6. A maize plant, and parts thereof, as claimed in claim 2, comprising the progeny of a cross between first and second inbred lines, genes conferring tolerance to high pH soil being present in the homozygous state in the genome of one or both of the said first and second inbred lines such that the genomes of said first and second inbreds together donate to the hybrid a complement of genes necessary to confer the tolerance to high pH soil.

7. A method for the production of an inbred maize plant according to claim 2 adapted for conferring, in hybrid combination with a suitable second inbred, tolerance to high pH soil, comprising:

(a) selecting a first donor parental line possessing the desired high pH tolerance at least having one of the loci 1–4 and crossing same with an elite, high yielding second parental line to produce a segregating plant population;

(b) screening the plant population for identified chromosomal loci of one or more genes associated with the tolerance to high pH soil trait; and (c) selecting plants from said population having said identified chromosomal loci for further crossing and selection, and repeating said crossing and selection until a line is obtained which is homozygous for the tolerance to high pH soil trait at sufficient loci to give tolerance to high pH in hybrid combination.

* * * * *